(12) United States Patent
Li et al.

(10) Patent No.: US 8,669,364 B2
(45) Date of Patent: Mar. 11, 2014

(54) TRIDENTATE PLATINUM (II) COMPLEXES

(71) Applicants: Jian Li, Phoenix, AZ (US); Zixing Wang, Shanghai (CN); Eric Turner, Phoenix, AZ (US)

(72) Inventors: Jian Li, Phoenix, AZ (US); Zixing Wang, Shanghai (CN); Eric Turner, Phoenix, AZ (US)

(73) Assignee: Arizona Board of Regents for and on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/745,111

(22) Filed: Jan. 18, 2013

(65) Prior Publication Data

US 2013/0137870 A1 May 30, 2013

Related U.S. Application Data

(62) Division of application No. 12/919,899, filed as application No. PCT/US2009/035441 on Feb. 27, 2009, now Pat. No. 8,389,725.

(60) Provisional application No. 61/032,818, filed on Feb. 29, 2008.

(51) Int. Cl.
*C07F 15/00* (2006.01)
*H01L 51/50* (2006.01)

(52) U.S. Cl.
USPC .............................. 546/2; 313/504; 428/690

(58) Field of Classification Search
USPC .............................. 546/2; 313/504; 428/690
See application file for complete search history.

(56) References Cited

U.S. PATENT DOCUMENTS

| | | | |
|---|---|---|---|
| 7,026,480 | B2 | 4/2006 | Che et al. |
| 7,029,766 | B2 | 4/2006 | Huo et al. |
| 7,166,368 | B2 | 1/2007 | Lecloux et al. |
| 7,276,617 | B2 | 10/2007 | Sotoyama et al. |
| 2002/0189666 | A1 | 12/2002 | Forrest et al. |
| 2006/0093854 | A1 | 5/2006 | Sotoyama et al. |
| 2006/0094875 | A1 | 5/2006 | Itoh et al. |
| 2007/0111025 | A1 | 5/2007 | Lennartz et al. |
| 2007/0224447 | A1 | 9/2007 | Sotoyama et al. |
| 2008/0067925 | A1 | 3/2008 | Oshiyama et al. |
| 2008/0269491 | A1 | 10/2008 | Jabbour et al. |
| 2011/0028723 | A1 | 2/2011 | Li et al. |
| 2011/0301351 | A1 | 12/2011 | Li et al. |

FOREIGN PATENT DOCUMENTS

| | | | |
|---|---|---|---|
| JP | 2006282965 A | 10/2006 | |
| JP | 2006114889 A1 | 4/2007 | |
| WO | WO0070655 A2 | 11/2000 | |
| WO | WO2004039781 A1 | 5/2004 | |
| WO | WO2005075600 A1 | 8/2005 | |
| WO | WO2005103195 A1 | 11/2005 | |
| WO | WO2005105746 A1 | 11/2005 | |
| WO | WO2006082742 A1 | 8/2006 | |
| WO | WO2006100888 A1 | 9/2006 | |
| WO | WO2009086209 A2 | 7/2009 | |
| WO | WO2009111299 A2 | 9/2009 | |

OTHER PUBLICATIONS

S. A. Willison et al., "A Luminescent Platinum(II) 2,6-Bis(N-pyrazolyl)pyridine Complex", Inorg. Chem. vol. 43, pp. 2548-2555, 2004.
J. M. Longmire et al., "Synthesis and X-ray Crystal Structures of Palladium(II) and Platinum(II) Complexes of the PCP-Type Chiral Tridentate Ligand", Organometallics, vol. 17, pp. 4374-4379, 1998.
V. Adamovich et al., "High efficiency single dopant white electrophosphorescent light emitting diodes", New J. Chem, vol. 26, pp. 1171-1178. 2002.
Del Cano et al., "Near-infrared electroluminescence based on perylenediimide-doped tris(8-quinolinolato)aluminum", Applied Physics Letters, 88, pp. 071117-1-071117-3, 2006.
B. Harrison et al., "Near-infrared electroluminescence from conjugated polymer/lanthanide porphyrin blends", Applied Physics Letter, vol. 79, No. 23, pp. 3770-3772, Dec. 3, 2001.
J. Kido et al., "Organo Lanthanide Metal Complexes for Electroluminescent Materials", Chem. Rev., vol. 102, pp. 2357-2368, 2002.
S. Lamansky et al., "Highly Phosphorescent Bis-Cyclometalated Iridium Complexes: Synthesis, Photophysical Characterization, and Use in Organic Light Emitting Diodes", J. Am. Chem. Soc., vol. 123, pp. 4304-4312, 2001.

(Continued)

*Primary Examiner* — Charanjit Aulakh
(74) *Attorney, Agent, or Firm* — Fish & Richardson P.C.

(57) ABSTRACT

A platinum (II) complex of general formula (II),

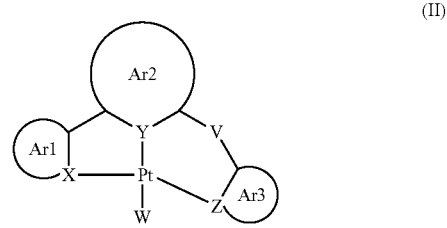

in which Ar1 is a 1,2-diazole ring, Ar2 is a pyridine ring, and Ar3 is a phenyl ring. Ar1, Ar2, and Ar3 together form a tridentate ligand coordinated to the platinum through atoms X, Y, and Z, respectively, and X, Y, and Z are independently carbon or nitrogen. V represents O, S, N, C, P, or Si, and W is an anion. In some cases, Ar3 is an anion and Ar1 and Ar2 are neutral; in other cases, Ar1 and Ar3 are neutral and Ar2 is an anion. The complexes emit in the UV to near IR range and are useful as emitters for organic light emitting devices.

7 Claims, 25 Drawing Sheets

(56) References Cited

OTHER PUBLICATIONS

S. Lamansky et al., "Synthesis and Characterization of Phosphorescent Cyclometalated Iridium Complexes", Inorg. Chem., vol. 40, pp. 1704-1711, 2001.
X. Li et al., "Synthesis and properties of novel poly(p-phenylenevinylene) copolymers for near-infrared emitting diodes", European Polymer Journal, vol. 41, pp. 2923-2933, 2005.
P. Peumans et al., "Small molecular weight organic thin-film photodetectors and solar cells", Journal of Applied Physics, vol. 93, No. 7, pp. 3693-3723, Apr. 1, 2003.
Rand et al., Organic Double-Heterostructure Photovoltaic Cells Employing Thick Tris (acetylacetonato) ruthenium(III) Exciton-Blocking Layers, Advanced Materials vol. 17, pp. 2714-2718, 2005.
C.W. Tang, "Two-layer organic photovoltaic cell", Appl. Phys. Letters 48 (2), pp. 183-185, 1986).
Vanhelmont et al., "Synthesis, Crystal Structure, High-Resolution Optical Spectroscopy, and Extended Huckel Calculations for [Re(CO)4(thpy)] (thpy-2-(2-Thienyl)pyridinate). Comparison with Related Cyclometalated Complexes", Inorg. Chem., vol. 36, pp. 5512-5517, 1997.
Williams et al., "Organic light-emitting diodes having exclusive near-infrared electrophosphorescence", Applied Physics Letters, vol. 89, pp. 083506 (3 pages), 2006.
Forrest et al., "Measuring the Efficiency of Organic Light-Emitting Devices", Advanced Materials, vol. 15, No. 13, pp. 1043-1048, 2003.
Cardenas et al., "Divergent Behavior of Palladium(II) and Platinum(II) in the Metalation of 1,2-Di(2-pyridyl)benzene," Organometallics 1999, 18, pp. 3337-3341.
Williams et al., "An Alternative Route to Highly Luminescent Platinum(II) Complexes," Inorg. Chem., 2003, 42, pp. 8609-8611.
Sanna et al., "Platinum complexes with N—N—C ligands. Synthesis, electrochemical and spectroscopic characteristics of platinum(II) and relevant electroreduced species," Inorganica Chimica Acta 305, 2000, pp. 189-205.
International Search Report and Written Opinion, PCT/US2008/087847, mailed Aug. 6, 2009, 12 pages.
International Search Report and Written Opinion, PCT/US20091035441, mailed Oct. 19, 2009, 14 pages.
Ionkin, A.S. et al.: Synthesis and structural characterization of a series of novel polyaromatic ligands containing pyrene and related biscyclometalated iridium complexes. Organometallics, vol. 25, pp. 1461-1471, 2006.

TRIDENTATE PLATINUM (II) COMPLEXES

CROSS-REFERENCE TO RELATED APPLICATIONS

This application is a divisional application of U.S. patent application Ser. No. 12/919,899, filed Aug. 27, 2010, which is the national stage application filed under 35 U.S.C. §371 of International Application No. PCT/US2009/035441, filed Feb. 27, 2009, which in turn claims priority to U.S. Provisional Patent Application Ser. No. 61/032,818 filed Feb. 29, 2008. The above applications are incorporated by reference herein.

TECHNICAL FIELD

This description relates to tridentate platinum (II) complexes and their use as emitters for organic light-emitting devices.

BACKGROUND

Organic light emitting devices (OLEDs) are a new generation of display technology. As depicted in FIG. 1, a typical OLED 100 includes a layer of indium tin oxide (ITO) as an anode 102, a single layer of hole-transporting materials (HTL) 104, a single layer of emissive materials (EML) 106 including emitter and host, a single layer of electron-transporting materials (ETL) 108 and a layer of metal cathode 110. The emission color of OLED is determined by the emission energy (optical energy gap) of emitters. Phosphorescent OLEDs (i.e., with phosphorescent materials as emitters) have higher device efficiency that fluorescent OLEDs (i.e., with fluorescent materials as emitters).

The development of efficient blue OLEDs is important for applications in displays, backlighting for displays and solid state lighting. The reported blue phosphorescent OLEDs use cyclometalated iridium complexes as emitters. These emitters require the supply of iridium, which is present in low abundance ($3 \times 10^{-6}$ ppm) in the Earth's crust.

SUMMARY

In one aspect, an asymmetric platinum (II) complex has general formula (I),

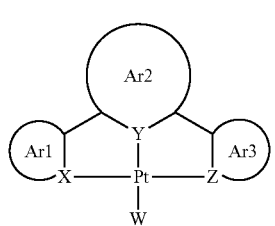

(I)

in which Ar1, Ar2, and Ar3 are each independently aryl, heteroaryl, or heterocyclic, and Ar1, Ar2, and Ar3 together form a tridentate ligand coordinated to the platinum through atoms X, Y, and Z, respectively. X, Y, and Z are independently carbon or nitrogen, and W is an anion.

In some implementations, W is a halogen, a cyano, alkyl, alkenyl, akynyl, alkoxy, alkylthio, amine, phosphine, or an optionally substituted aryl or heteroaryl group. Examples of W are shown in FIG. 5, in which U represents O, S, or N—R, and each W is unsubstituted, or substituted and/or optionally substituted with one more R groups. As defined herein, each R group independently represents an alkyl group, a haloalkyl group, an aralkyl group, an alkenyl group, alkynyl group, an aryl group, an amino group, a mono- or di-alkylamino group, a mono- or diaryl amino group, an alkoxy group, an aryloxy group, a heteroaryloxy group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, an ureido group, a phosphoramide group, a hydroxyl group, a mercapto group, a halogen atom, a cyano group, a sulfo group, a carboxyl group, a nitro group, a hydrazino group, a substituted silyl group, or a polymerizable group.

In some implementations, Ar1 and W are anions and Ar2 and Ar3 are neutral.

Examples of Ar1 are shown in FIG. 2, where each Ar1 is unsubstituted or substituted with one or more R groups, and U and R are as defined above.

Examples of Ar2 are shown in FIG. 3, where each Ar2 is unsubstituted or substituted with one or more R groups, and U and R are as defined above.

Examples of Ar3 are shown in FIG. 4, where each Ar3 is unsubstituted or substituted with one or more R groups, and U and R are as defined above.

Examples of complexes with general formula (I) are shown FIG. 6, where Ph is phenyl or tert-butylphenyl.

In some implementations, Ar1 and Ar3 are neutral, and Ar2 and W are anions.

In some implementations, Ar1 and Ar3 have a different molecular structure. Examples of Ar1 and Ar3 are shown in FIG. 7, where each Ar1 and Ar3 is unsubstituted or substituted with one or more R groups, and U and R are as defined above.

Examples of Ar2 are shown in FIG. 8, where each Ar2 is unsubstituted or substituted with one or more R groups, and U and R are as defined above.

Additional examples of complexes of general formula (I) are shown in FIG. 9, where Ph represents phenyl or tert-butylphenyl.

In another aspect, an asymmetric platinum (II) complex has general formula (II),

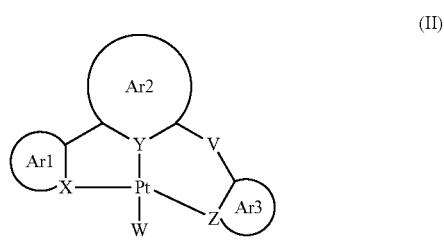

(II)

in which Ar1, Ar2, and Ar3 are each independently aryl, heteroaryl, or heterocyclic, and Ar1, Ar2, and Ar3 together form a tridentate ligand coordinated to the platinum through atoms X, Y, and Z, respectively. X, Y, and Z are independently carbon or nitrogen, and W is an anion. In some cases, —V— is a covalent bond (i.e., general formula (II) becomes general formula (I)). In other cases —V— is a bridging group including functional groups such as, for example,

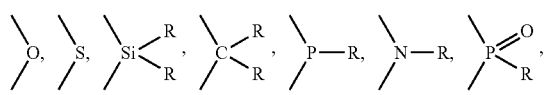

and derivatives thereof, in which R is as defined above.

In some implementations, W is a halogen, a cyano, alkyl, alkenyl, akynyl, alkoxy, alkylthio, amine, phosphine, or an optionally substituted aryl or heteroaryl group. Examples of W are shown in FIG. 5, in which U represents O, S, or N—R, and each W is unsubstituted, or substituted and/or optionally substituted with one more R groups. As defined herein, each R group independently represents an alkyl group, a haloalkyl group, an aralkyl group, an alkenyl group, alkynyl group, an aryl group, an amino group, a mono- or di-alkylamino group, a mono- or diaryl amino group, an alkoxy group, an aryloxy group, a heteroaryloxy group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, an ureido group, a phosphoramide group, a hydroxyl group, a mercapto group, a halogen atom, a cyano group, a sulfo group, a carboxyl group, a nitro group, a hydrazino group, a substituted silyl group, or a polymerizable group.

In some implementations, Ar3 and W are anions and Ar1 and Ar2 are neutral.

Examples of Ar1 are shown in FIG. 4, where each Ar1 is unsubstituted or substituted with one or more R groups, and U and R are as defined above.

Examples of Ar2 are shown in FIG. 3, where each Ar2 is unsubstituted or substituted with one or more R groups, and U and R are as defined above.

Examples of Ar3 are shown in FIG. 2, where each Ar3 is unsubstituted or substituted with one more R groups, and U and R are as defined above.

Examples of asymmetric platinum (II) complexes of general formula (II) are shown in FIG. 10, where Ph represents phenyl or tert-butylphenyl.

In some implementations, Ar1 and Ar3 are neutral, and Ar2 and W are anions.

In some implementations, Ar1 and Ar3 have a different molecular structure. Examples of Ar1 and Ar3 are shown in FIG. 7, where each Ar1 and Ar2 is unsubstituted or substituted with one or more R groups, and U and R are as defined above.

Examples of Ar2 are shown in FIG. 8, where each Ar2 is unsubstituted or substituted with one or more R groups, and U and R are as defined above.

Examples of the asymmetric platinum (II) complex are shown in FIG. 11, where Ph represents phenyl or tert-butylphenyl.

In one aspect, a phosphorescent emitter includes an asymmetric platinum (II) complex described above.

In one aspect, an organic light emitting device includes an asymmetric platinum (II) complex described above.

DETAILED DESCRIPTION

Figure 1:
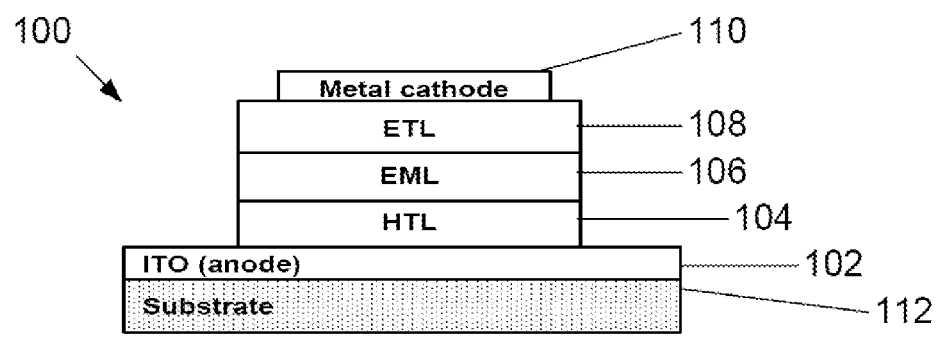
FIG. 1 depicts an organic light emitting device (OLED).
Figure 2:
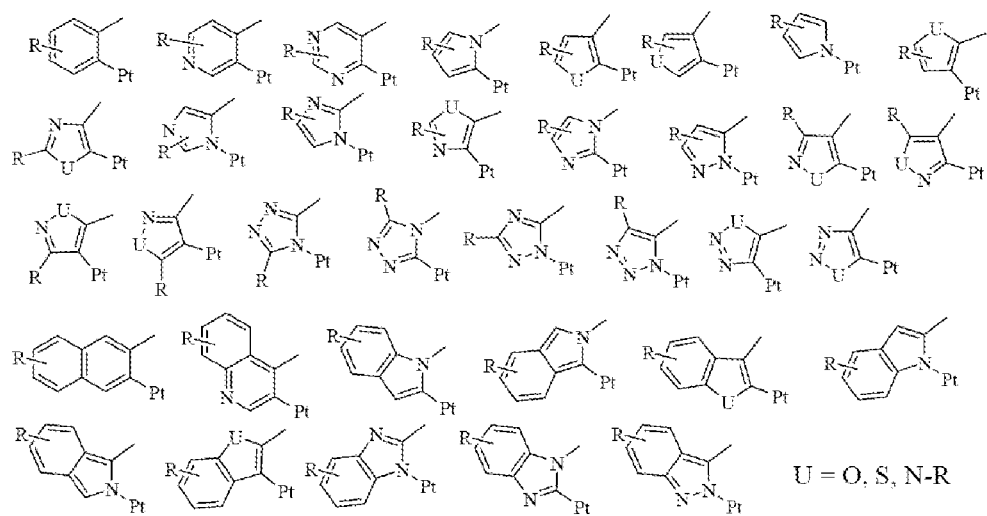
FIG. 2 depicts structures of anionic groups that form a side portion of an asymmetric tridentate ligand for a Pt(II) complex.
Figure 3:
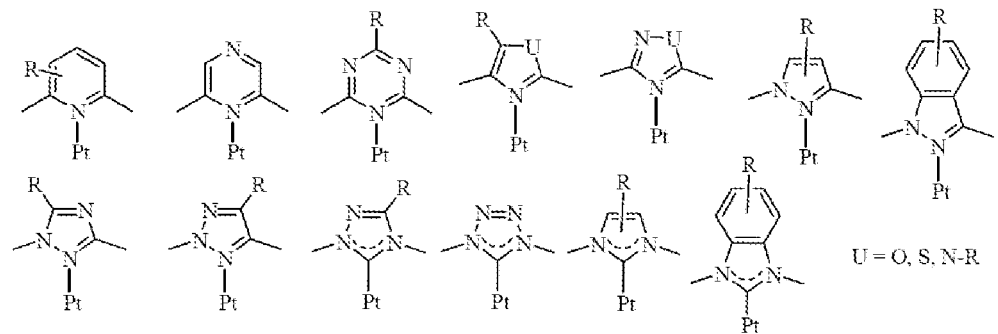
FIG. 3 depicts structures of neutral groups that form a central portion of a tridentate ligand for a Pt(II) complex.
Figure 4:
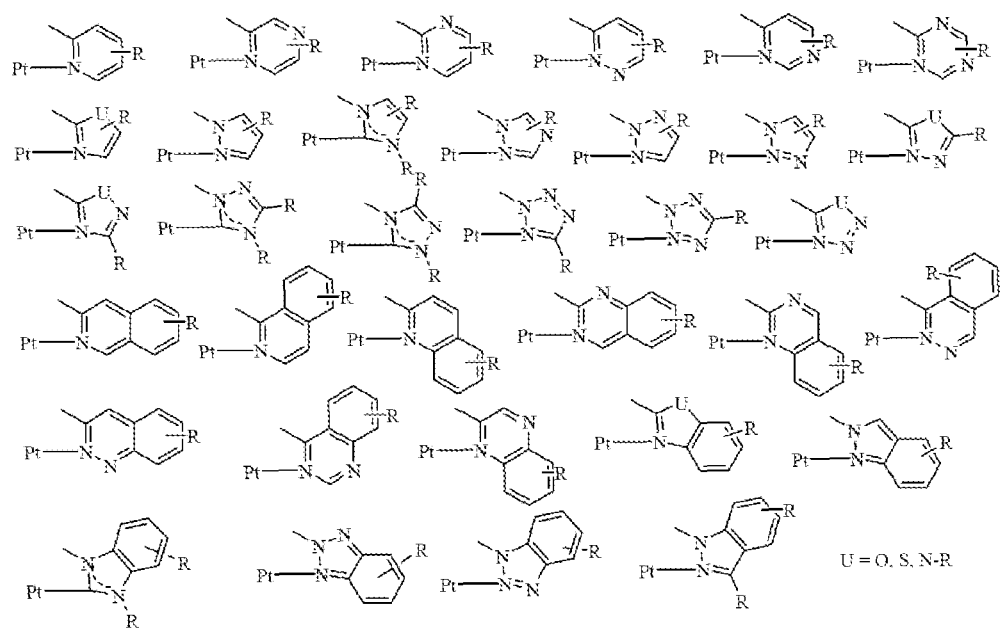
FIG. 4 depicts structures of neutral groups that form a side portion of a tridentate ligand for a Pt(II) complex.
Figure 5:
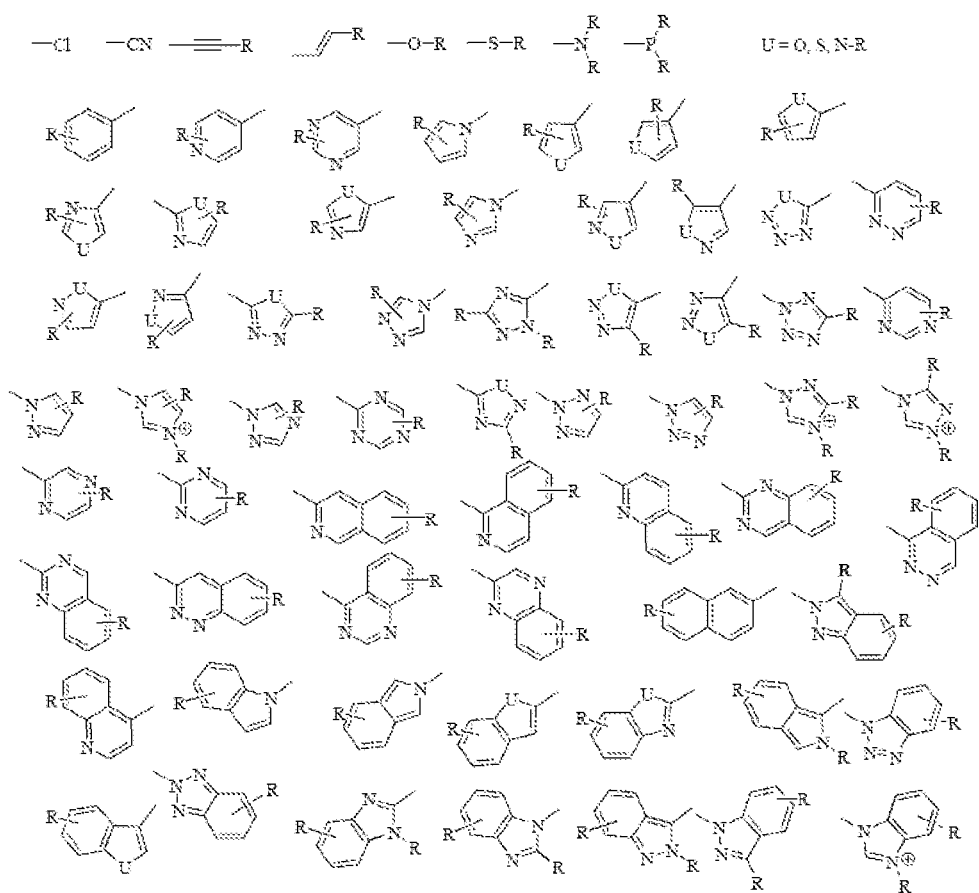
FIG. 5 depicts anionic ligands W for a Pt(II) complex.

Asymmetric tridentate platinum (II) complexes of general formula (I)

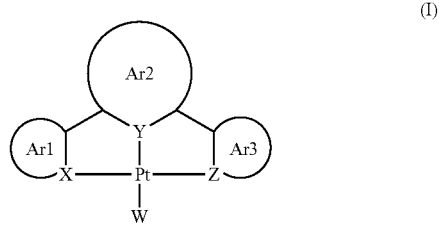

(I)

are described herein. The asymmetric complexes include a tridentate ligand with Ar1, Ar2, and Ar3 coordinated to the platinum through carbon or nitrogen atoms X, Y, and Z, respectively. Monodentate ligand W is also coordinated to the platinum. These complexes are phosphorescent, and feature emission energies in a wide range between UV and near IR, with intense emission in the blue region of the visible spectrum. The asymmetric nature of these complexes and the identity of the ligands allow emission energies and thermal properties (e.g., sublimation temperature and thermal decomposition temperature) of the complexes to be tuned based on the selection of the coordinating ligands. The asymmetric tridentate platinum (II) complexes described herein can be used as luminescent labels, emitters for organic light emitting diodes (OLEDs), absorbers for solar cells, color conversion materials, and other applications, such as organic electroluminescent elements and lighting equipment.

In general formula (I), Ar1, Ar2, and Ar3 function as either anionic or neutral portions of a tridentate ligand. Ar1, Ar2, and Ar3 are each independently aryl, heteroaryl, or heterocyclic, with atom X, Y, and Z, respectively, coordinated to the platinum, where X, Y, and Z are independently carbon or nitrogen. W represents a halogen atom, or a cyano, alkyl, alkenyl, akynyl, alkoxy, alkylthio, amine, or phosphine group, or an optionally substituted aryl or heteroaryl group. W can be coordinated to the platinum through, for example, a carbon (C), oxygen (O), sulfur (S), nitrogen (N), or phosphorus (P) atom. In one aspect, Ar1 and W are anions, and Ar2 and Ar3 are neutral. In another aspect, Ar1 and Ar3 are neutral with different molecular structures, and Ar2 and W are anions.

FIGS. 2-5 depict examples of structures of

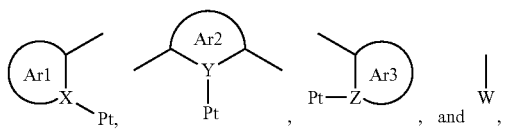

respectively, for the embodiment in which Ar1 and W are anions, and Ar2 and Ar3 are neutral. In FIGS. 2-5, U represents O, S, or N—R. Additionally, as indicated in FIGS. 2-5, certain structures are unsubstituted (no R present in the structure), substituted (R depicted as bonded to a particular atom in a structure), or optionally substituted (R depicted as extending from an aryl, heteroaryl, or heterocyclic group without a bond to a particular atom in the group) with one or more R groups. Each R independently represents an alkyl group, a haloalkyl group, an aralkyl group, an alkenyl group, alkynyl group, an aryl group, an amino group, a mono- or di-alkylamino group, a mono- or diaryl amino group, an alkoxy group, an aryloxy group, a heteroaryloxy group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, an ureido group, a phosphoramide group, a hydroxyl group, a mercapto group, a halogen atom, a cyano group, a sulfo group, a carboxyl group, a nitro group, a hydrazino group, a substituted silyl group, or a polymerizable group.

Figure 6:
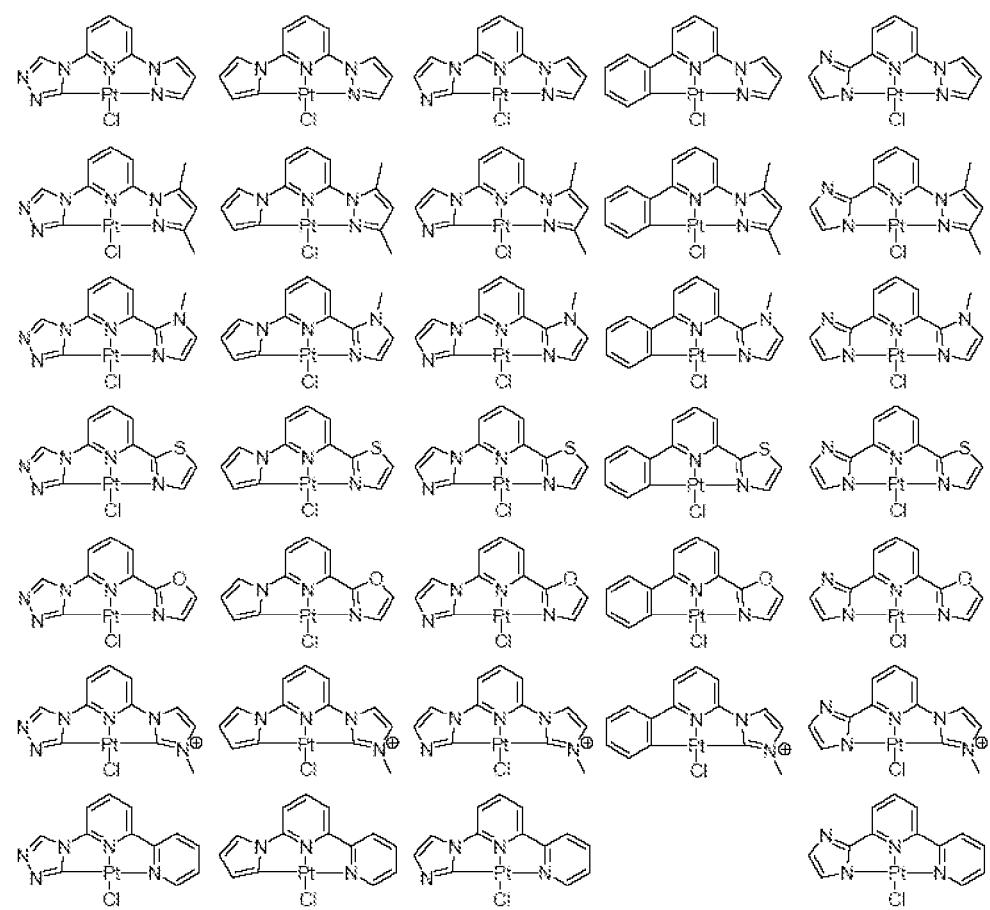
FIG. 6 depicts structures of asymmetric Pt(II) complexes shown in general formula (I) with anionic Ar1 and W groups and neutral Ar2 and Ar3 groups.
Figure 6:
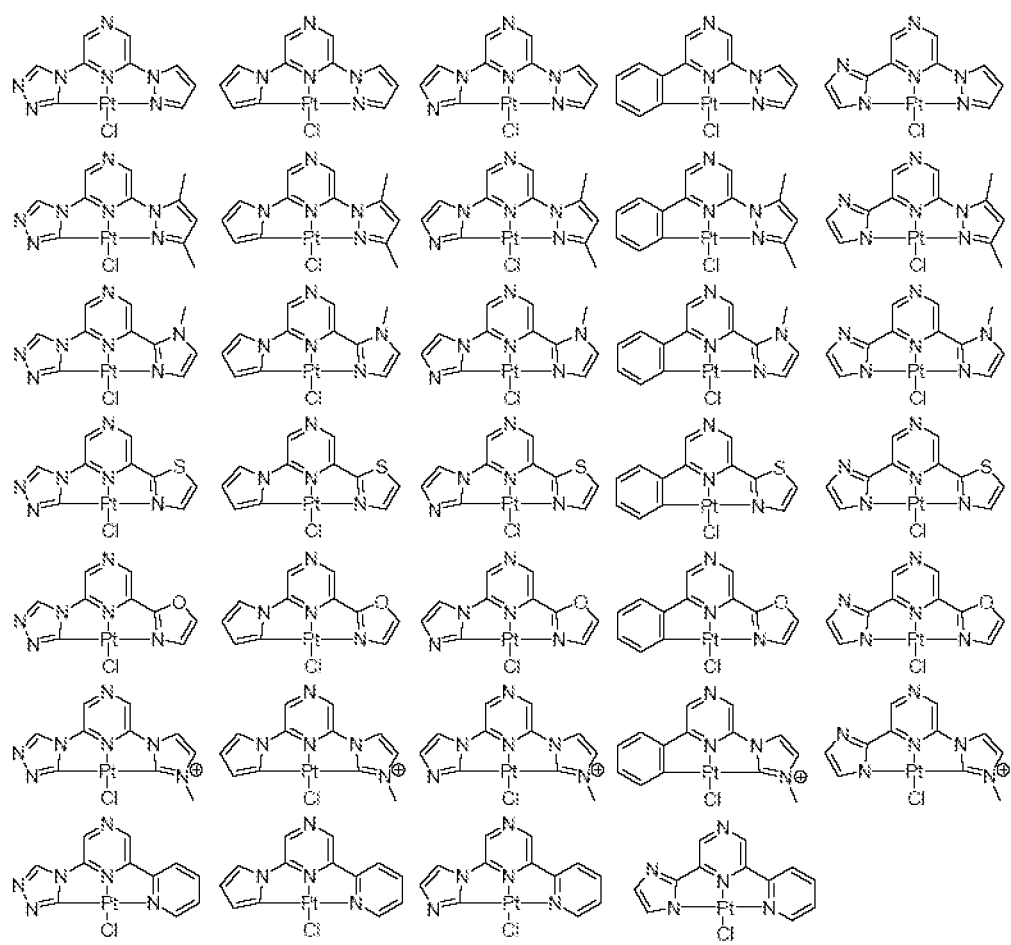
Figure 6:
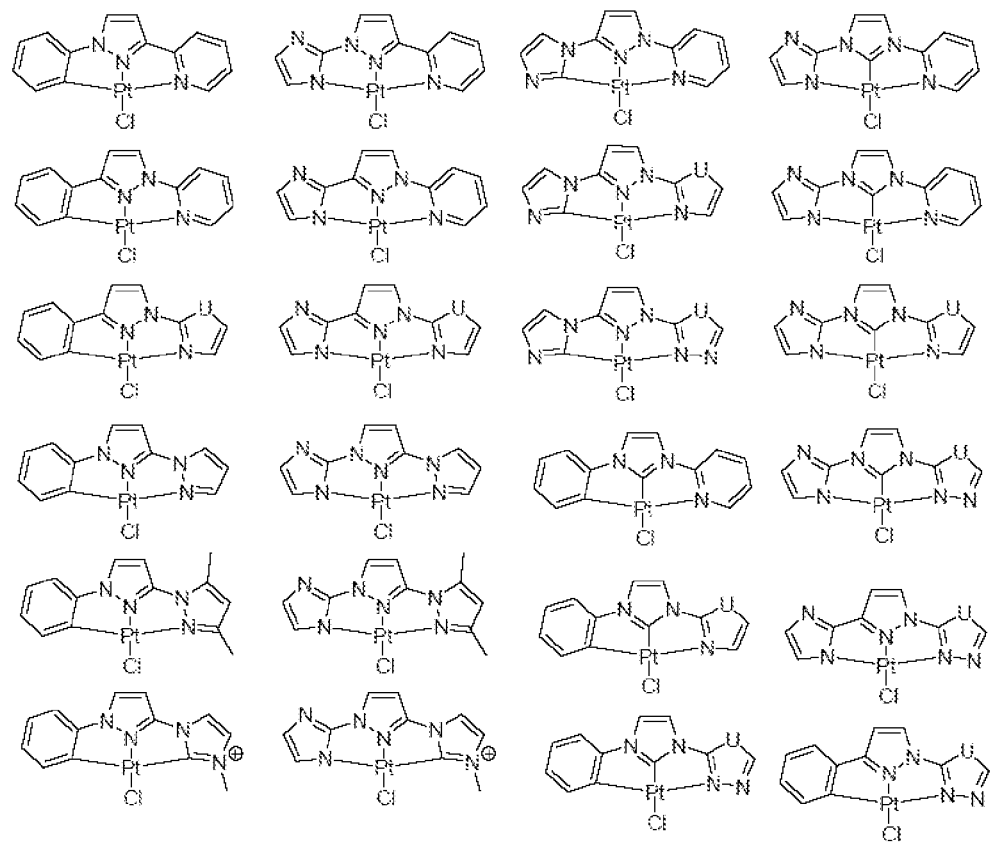
Figure 6:
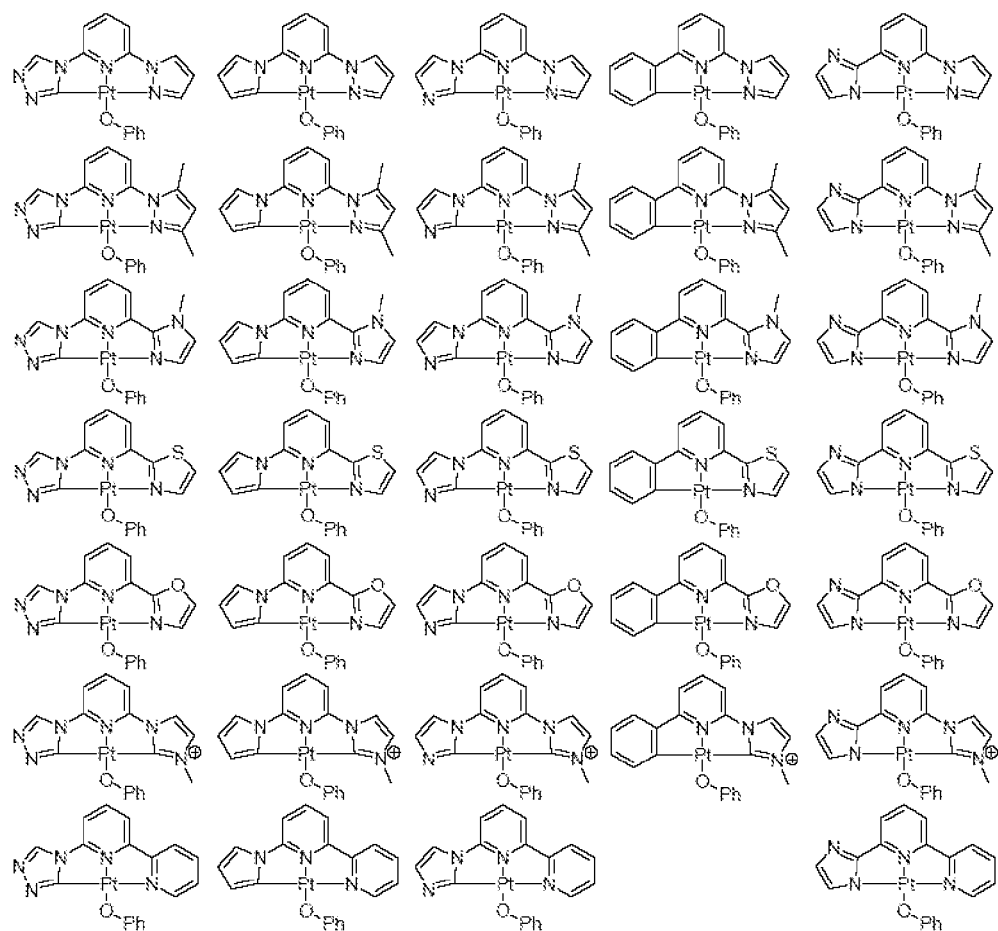
Figure 6:
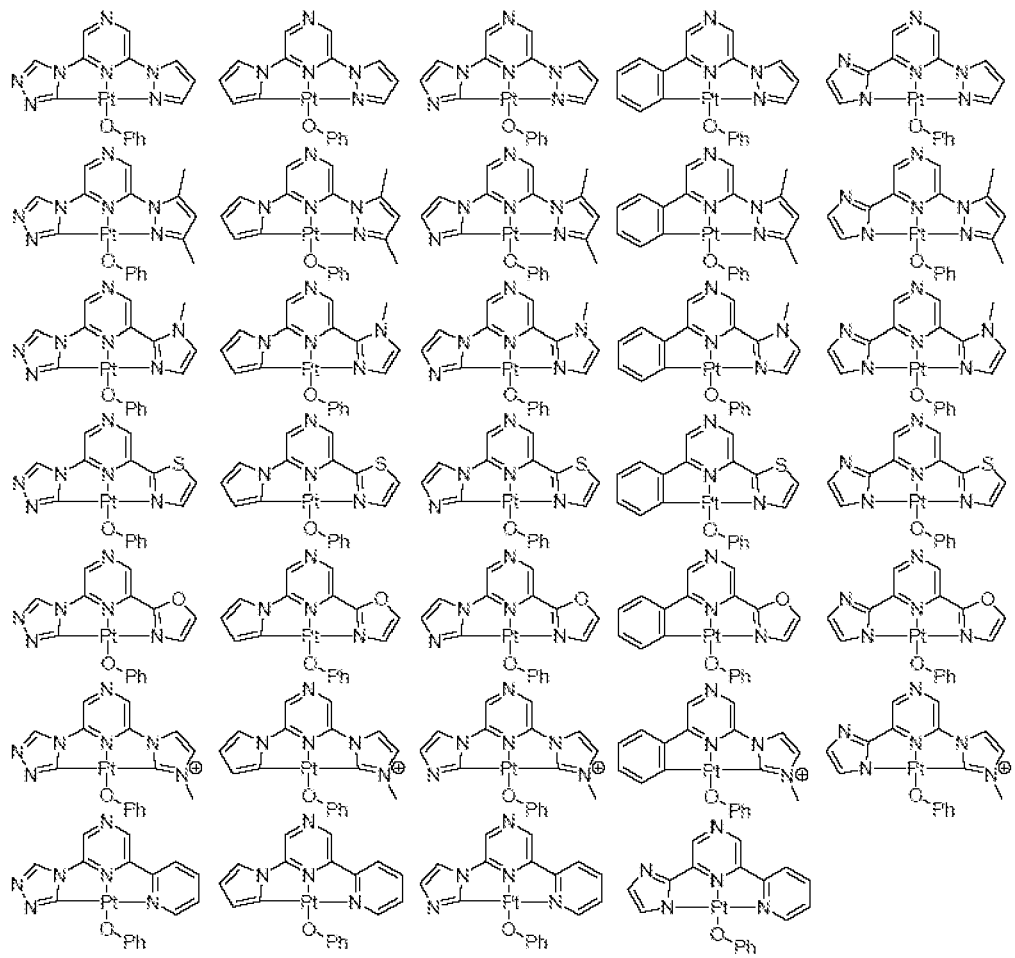
Figure 6:
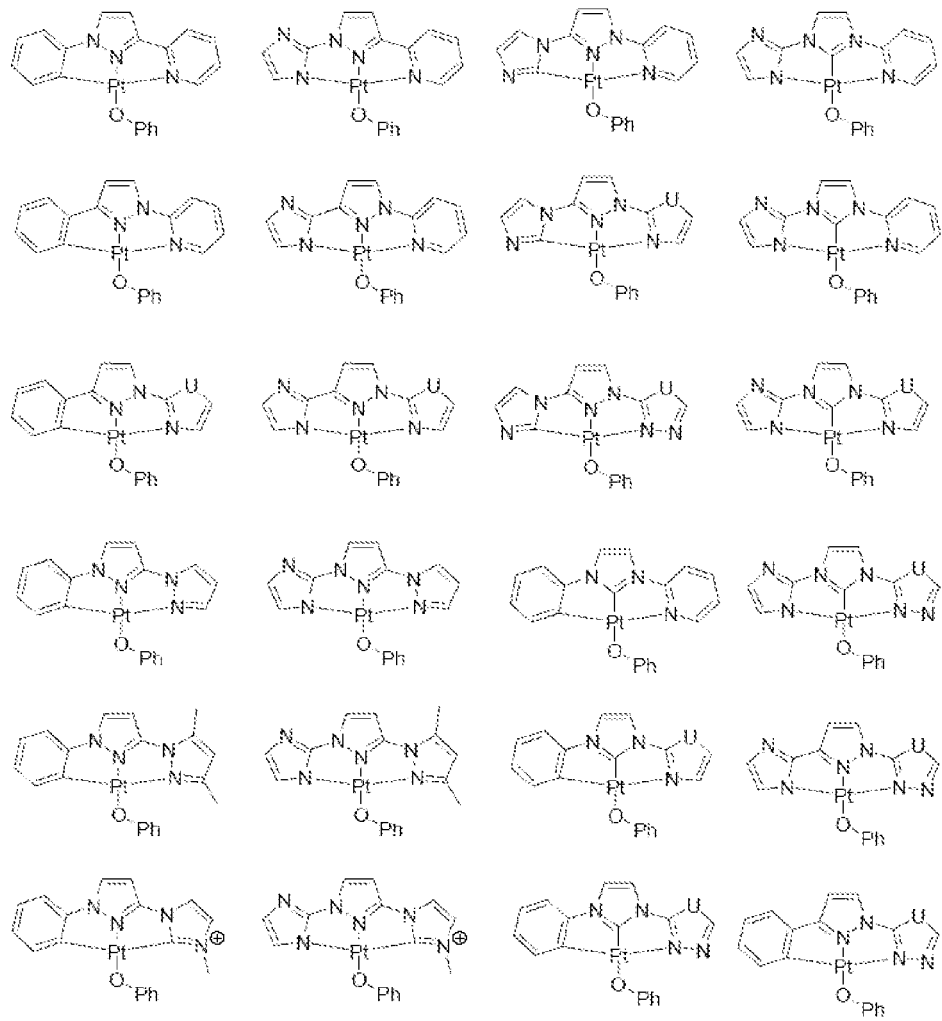

FIG. 6 depicts examples of structures of general formula (I) for the case in which Ar1 and W are anions, and Ar2 and Ar3 are neutral. In FIG. 6, Ph represents phenyl or tert-butylphenyl.

Figure 7:
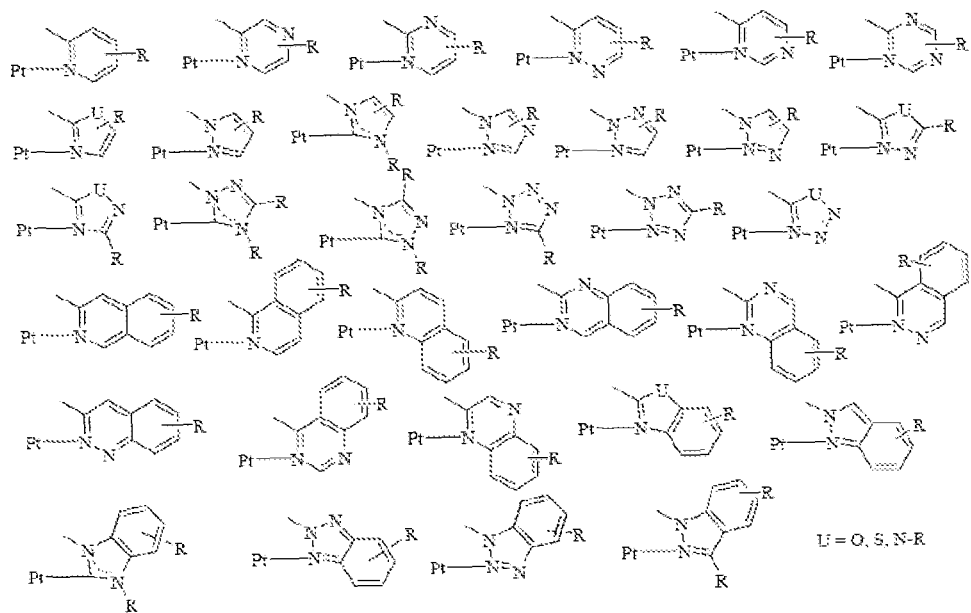
FIG. 7 depicts structures of neutral groups that form side portions of a tridentate ligand for a Pt(II) complex.

FIG. 7 depicts examples of structures of

Figure 8:
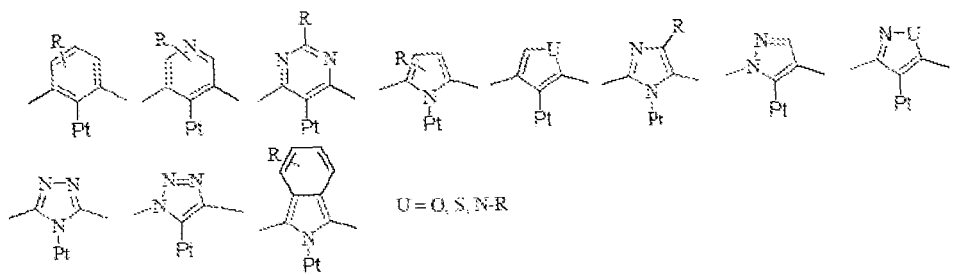
FIG. 8 depicts structures of anionic groups that form a side portion of a tridentate ligand for a Pt(II) complex.

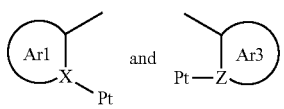

for the embodiment in which Ar1 and Ar3 are neutral. FIG. 8 depicts examples of structures of

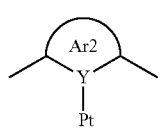

for the embodiment in which Ar2 and W are anions. In FIGS. 7 and 8, U represents O, S, or N—R. Additionally, as indicated in FIGS. 7 and 8, certain structures are substituted or optionally substituted with one or more R groups, as defined above.

Figure 9:
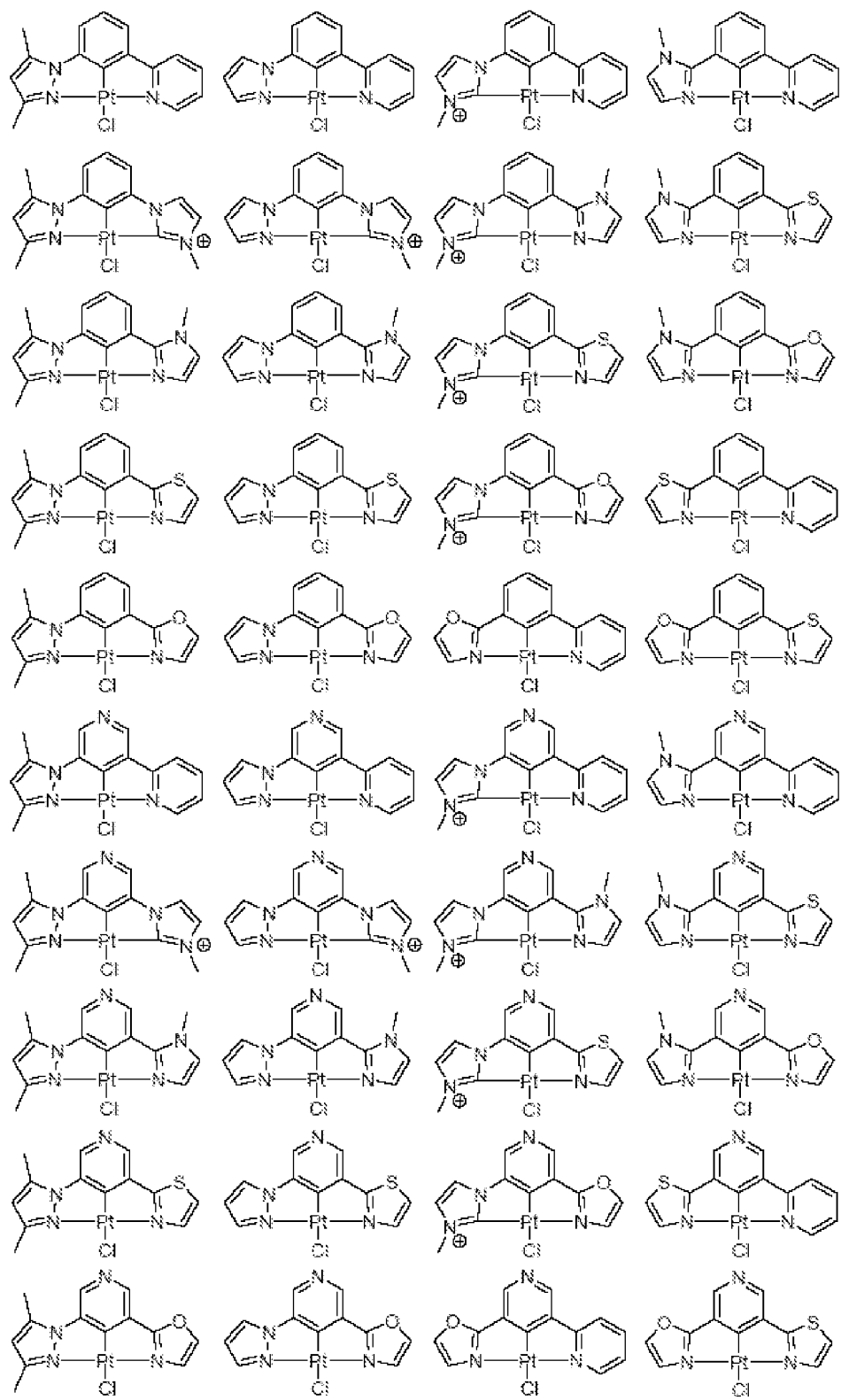
FIG. 9 depicts structures of asymmetric tridentate Pt(II) complexes shown in general formula (I) with neutral Ar1 and Ar3 groups and anionic Ar2 and W groups.
Figure 9:
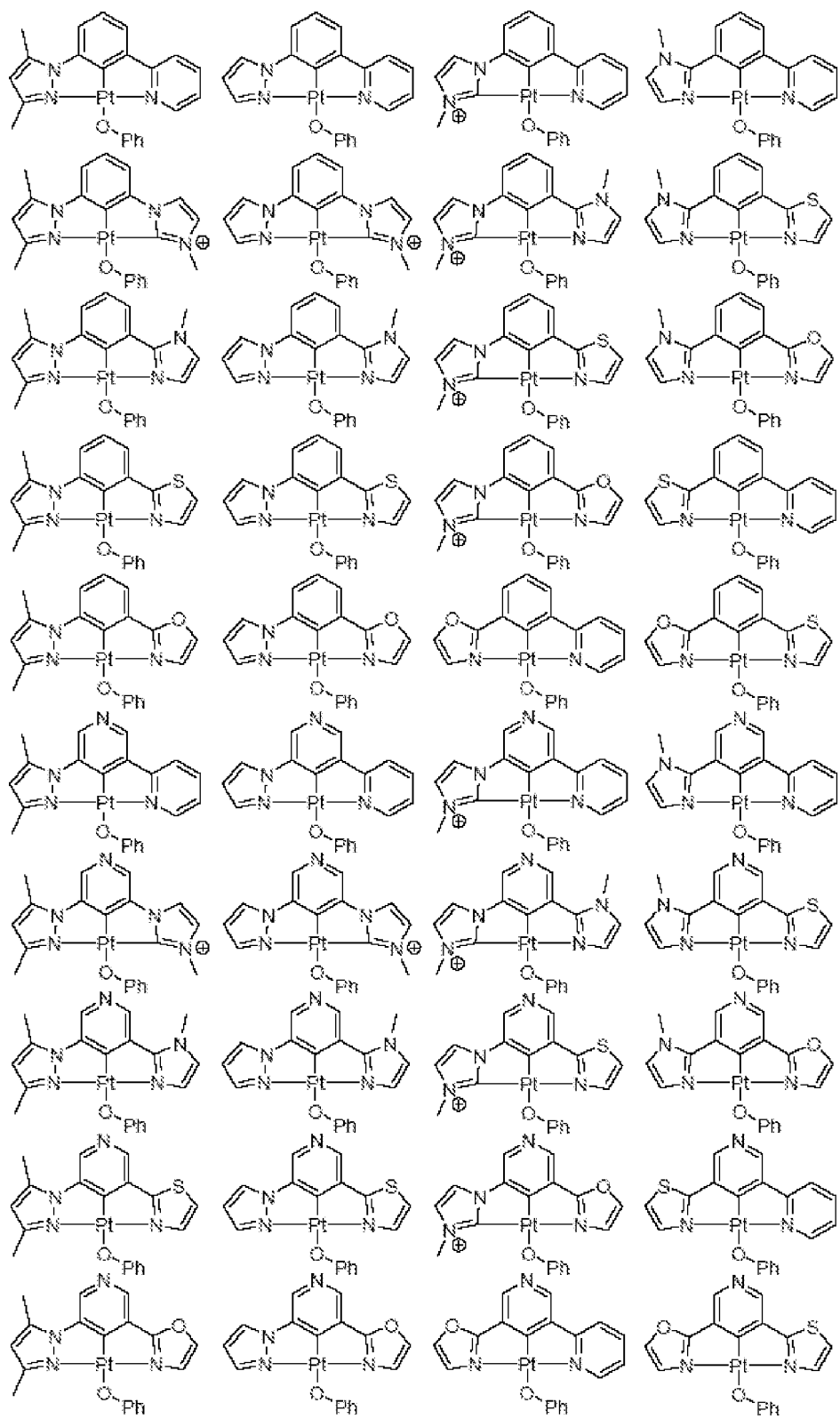
Figure 9:
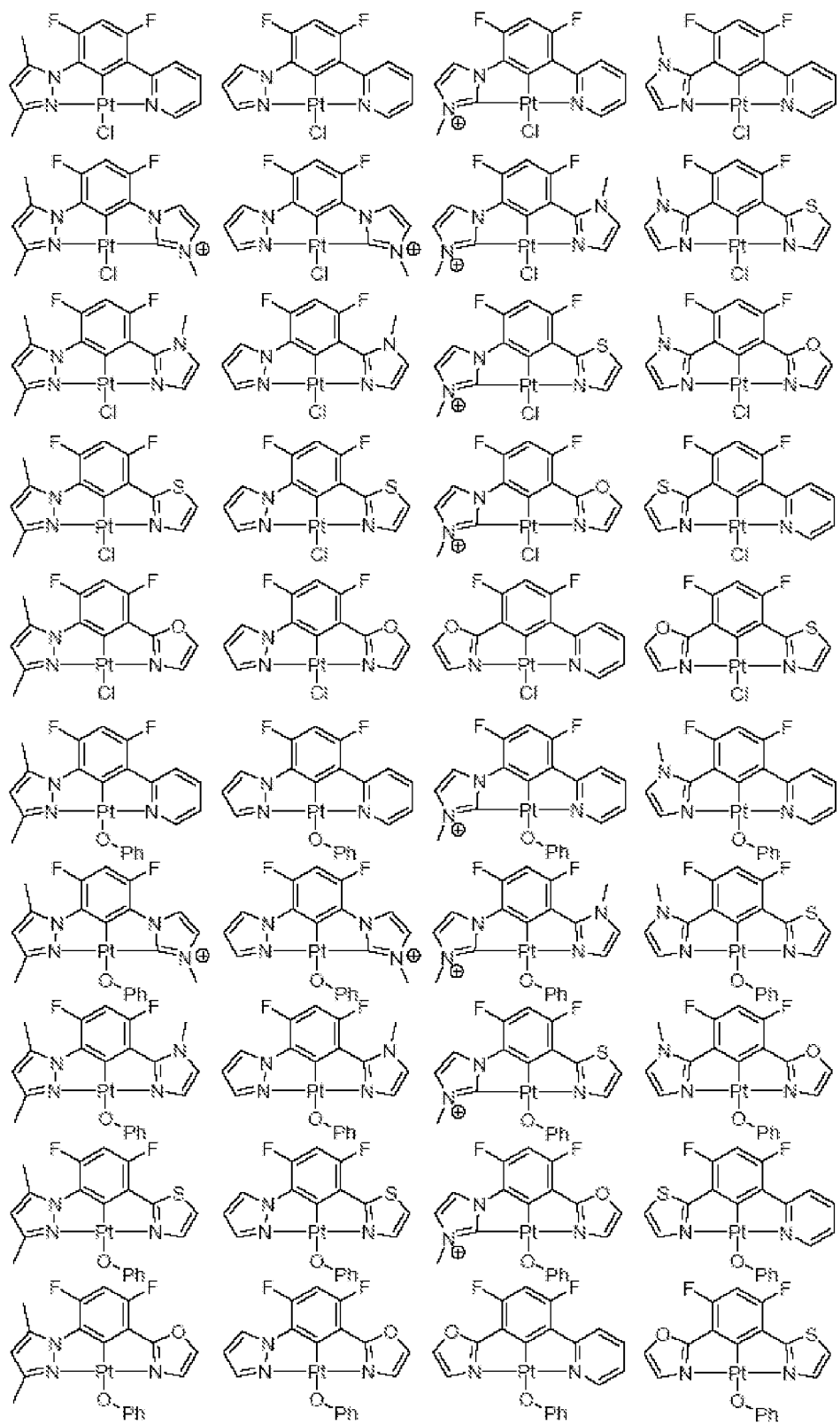
Figure 9:
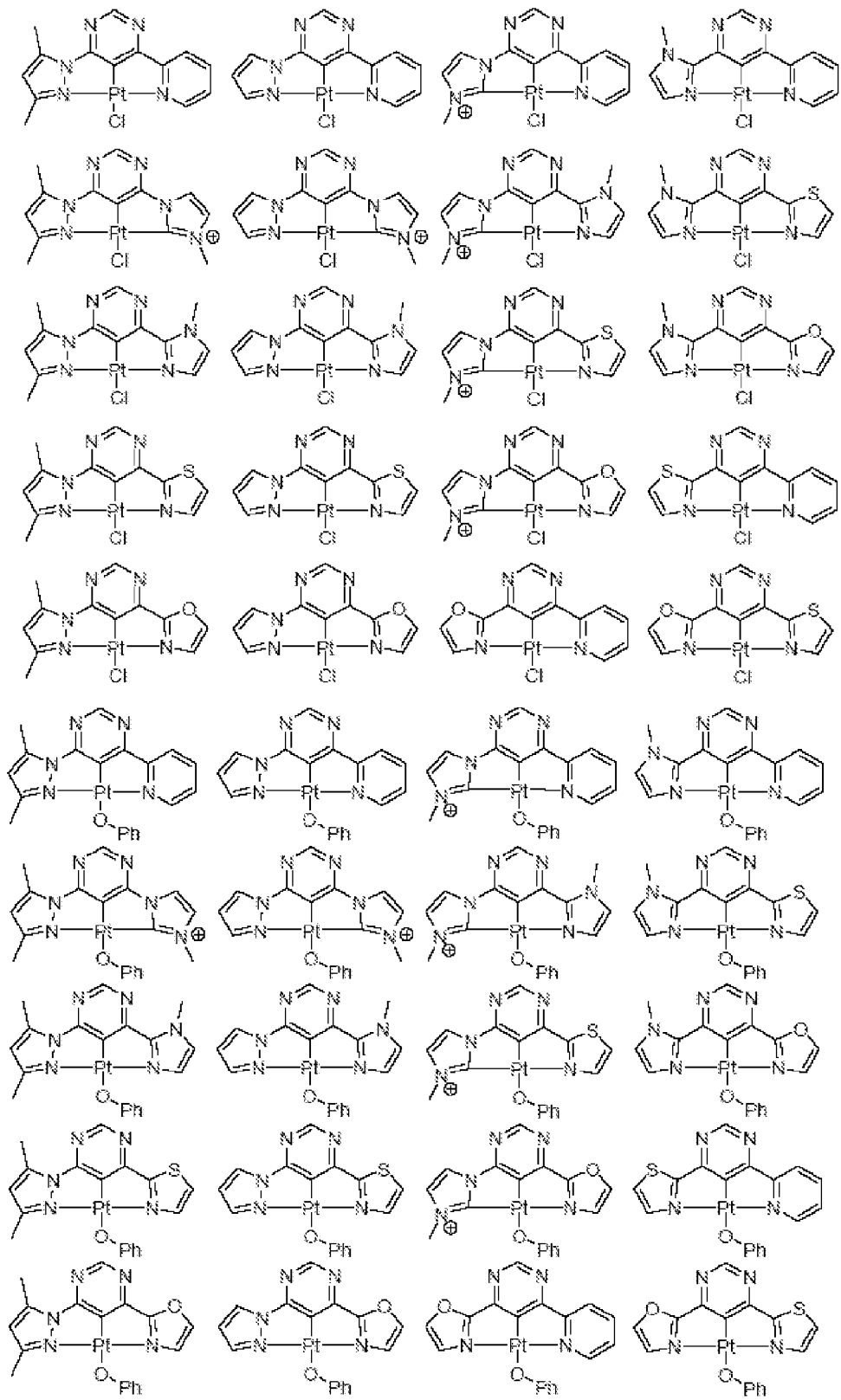
Figure 9:
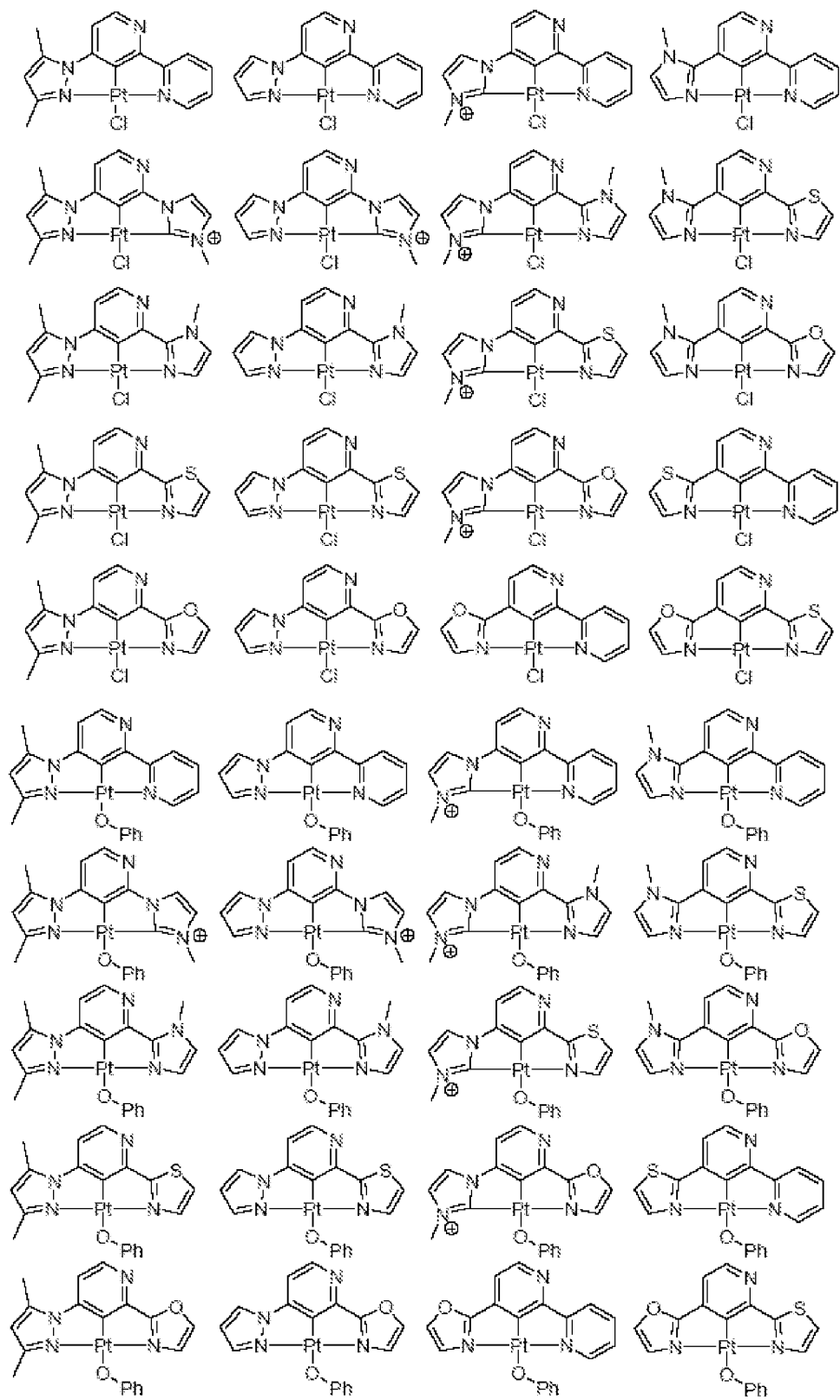

FIG. 9 depicts examples of asymmetric tridentate platinum (II) complexes of general formula (I), where Ar1 and Ar3 are neutral and have different molecular structures, and Ar2 and W are anions.

Asymmetric tridentate platinum (II) complexes of general formula (II)

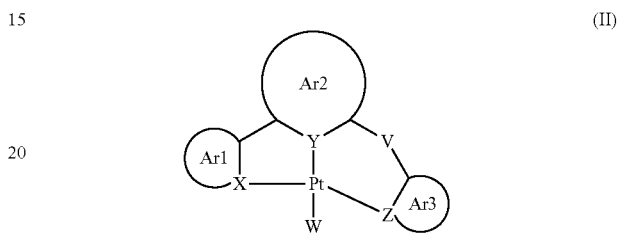

are described herein. The asymmetric complexes include a tridentate ligand with Ar1, Ar2, and Ar3 coordinated to the platinum through carbon or nitrogen atoms X, Y, and Z, respectively. In some cases, —V— is a covalent bond, such that general formula (II) satisfies general formula (I). In some cases, —V— is a bridging group including functional groups such as, for example,

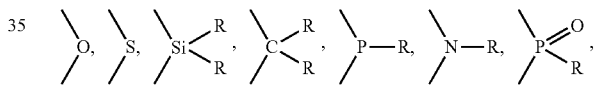

and derivatives thereof. Monodentate ligand W is also coordinated to the platinum. These complexes are phosphorescent, and feature emission energies in a wide range between UV and near IR, with intense emission in the blue region of the visible spectrum. The asymmetric nature of these complexes and the identity of the ligands allow emission energies and thermal properties (e.g., sublimation temperature and thermal decomposition temperature) of the complexes to be tuned based on the selection of the coordinating ligands. The asymmetric tridentate platinum (II) complexes described herein can be used as luminescent labels, emitters for organic light emitting diodes (OLEDs), absorbers for solar cells, color conversion materials, and other applications, such as organic electroluminescent elements and lighting equipment.

In general formula (II), Ar1, Ar2, and Ar3 function as either anionic or neutral portions of a tridentate ligand. Ar1, Ar2, and Ar3 are each independently aryl, heteroaryl, or heterocyclic, with atom X, Y, and Z, respectively, coordinated to the platinum, where X, Y, and Z are independently carbon or nitrogen. W represents a halogen atom, or a cyano, alkyl, alkenyl, akynyl, alkoxy, alkylthio, amine, or phosphine group, or an optionally substituted aryl or heteroaryl group. W can be coordinated to the platinum through, for example, a carbon (C), oxygen (O), sulfur (S), nitrogen (N), or phosphorus (P) atom. In one aspect, Ar3 and W are anions, and Ar2 and Ar3 are neutral. In another aspect, Ar1 and Ar3 are neutral with different molecular structures, and Ar2 and W are anions.

FIGS. 2-5 depict examples of structures of

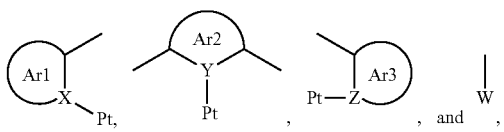

respectively, for the embodiment in which Ar3 and W are anions, and Ar1 and Ar2 are neutral. In FIGS. 2-5, U represents O, S or N—R. Additionally, as indicated in FIGS. 2-5, certain structures are unsubstituted (no R present in the structure), substituted (R depicted as bonded to a particular atom in a structure), or optionally substituted (R depicted as extending from an aryl, heteroaryl, or heterocyclic group without a bond to a particular atom in the group) with one or more R groups. Each R independently represents an alkyl group, a haloalkyl group, an aralkyl group, an alkenyl group, alkynyl group, an aryl group, an amino group, a mono- or di-alkylamino group, a mono- or diaryl amino group, an alkoxy group, an aryloxy group, a heteroaryloxy group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, an ureido group, a phosphoramide group, a hydroxyl group, a mercapto group, a halogen atom, a cyano group, a sulfo group, a carboxyl group, a nitro group, a hydrazino group, a substituted silyl group, or a polymerizable group.

Figure 10:
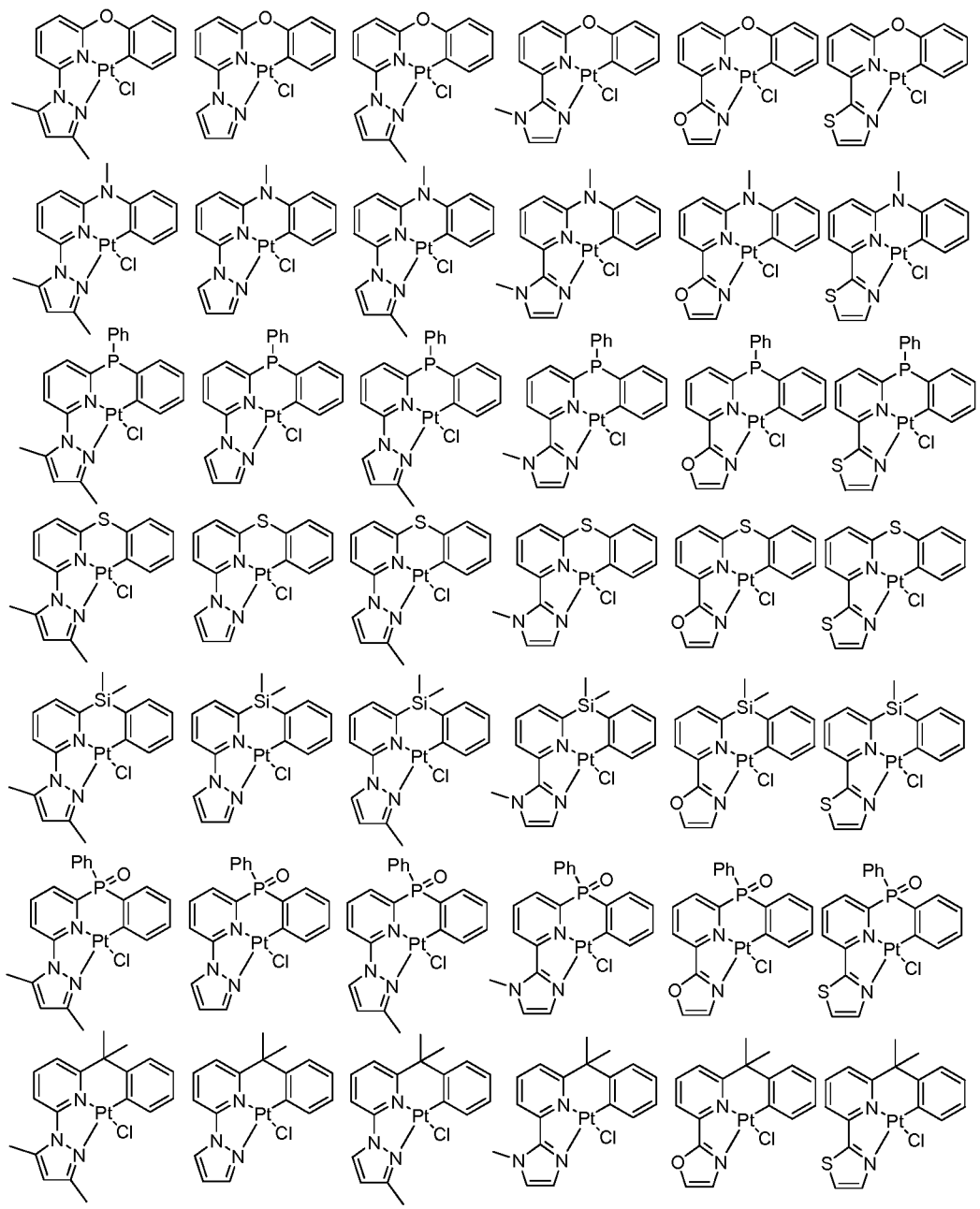
FIG. 10 depicts structures of asymmetric tridentate Pt(II) complexes shown in general formula (II).
Figure 10:
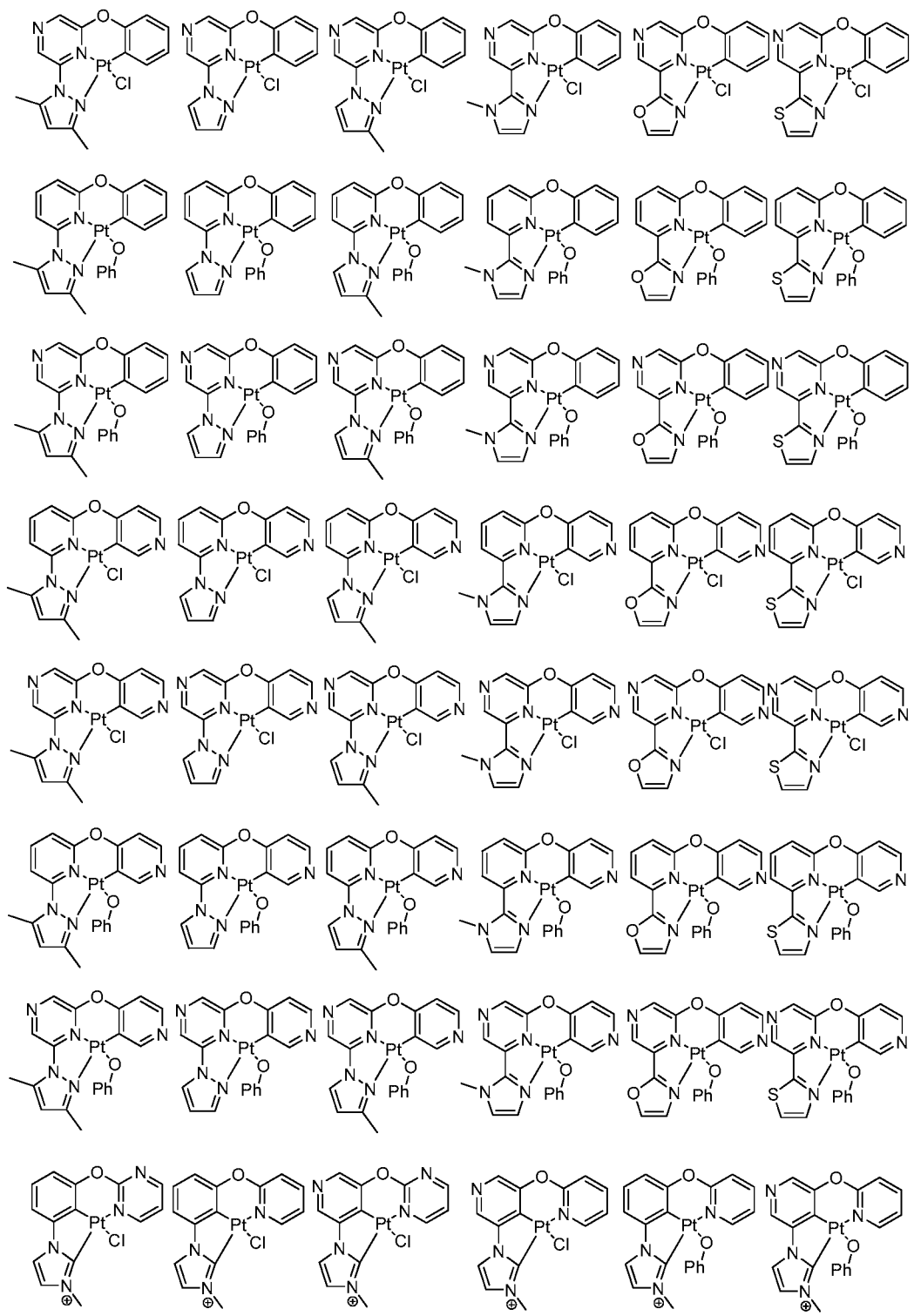

FIG. 10 depicts examples of structures of general formula (II) for the case in which Ar3 and W are anions, and Ar1 and Ar2 are neutral. In FIG. 10, Ph represents phenyl or tert-butylphenyl.

FIG. 7 depicts examples of structures of

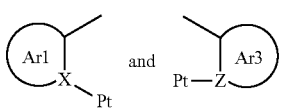

for the embodiment in which Ar1 and Ar3 are neutral. FIG. 8 depicts examples of structures of

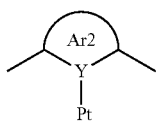

for the embodiment in which Ar2 and W are anions. In FIGS. 7 and 8, U represents O, S, or N—R. Additionally, as indicated in FIGS. 7 and 8, certain structures are substituted or optionally substituted with one or more R groups, as defined above.

Figure 11:
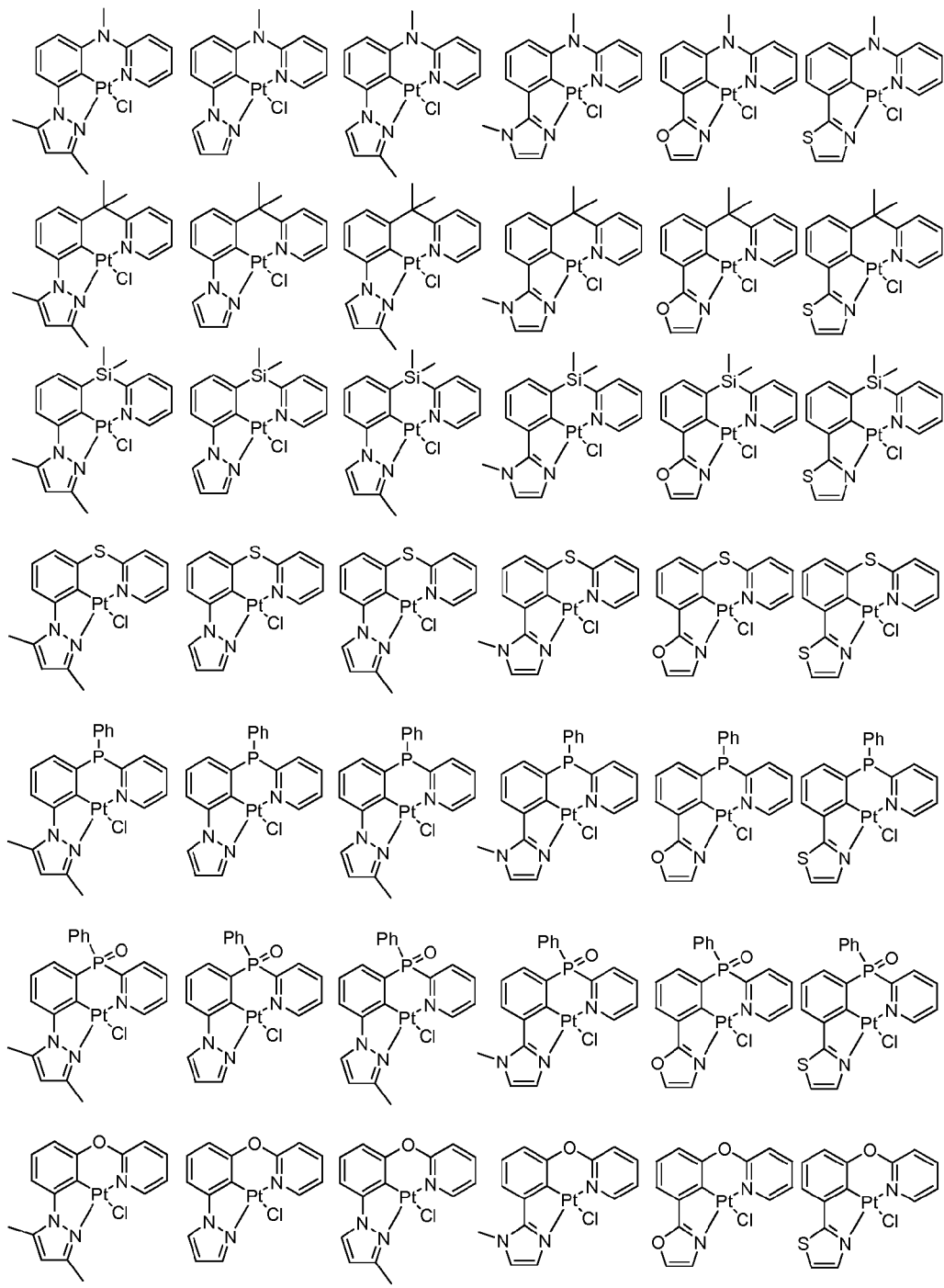
FIG. 11 depicts structures of asymmetric tridentate Pt(II) complexes shown in general formula (II).
Figure 11:
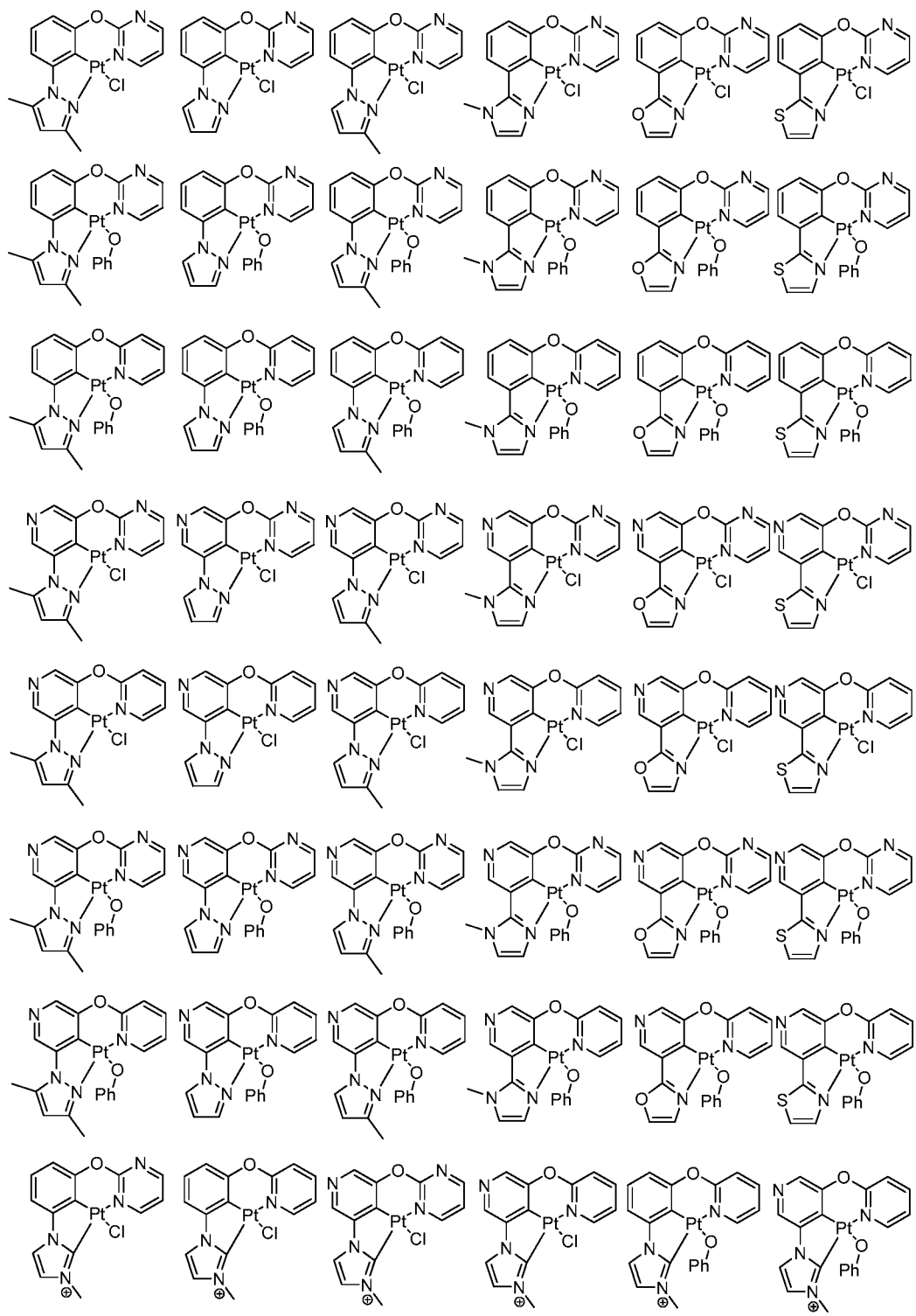

FIG. 11 depicts examples of structures of general formula (II) for the case in which Ar2 and W are anions, and Ar1 and Ar3 are neutral. In FIG. 11, Ph represents phenyl or tert-butylphenyl.

EXAMPLES

The following examples describe synthesis of a variety of compounds discussed above.

Example 1

Synthesis of DMPz-Ph-Py-PtCl

Synthesis of DMPz-Ph-I

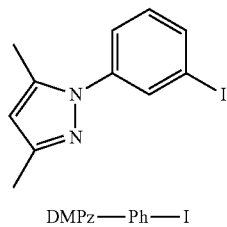

DMPz—Ph—I

After standard cycles of evacuation and back-fill with dry and pure nitrogen, an oven-dried Schlenk flask equipped with a magnetic stir bar was charged with $Cu_2O$ (0.1 mmol, 10 mol %), syn-2-pyridinealdoxime (0.4 mmol, 20 mol %), 3,5-dimethylpyrazole (1.1 mmol), $Cs_2CO_3$ (2.5 mmol), 1,3-diiodobenzene (1.0 mmol), and anhydrous and degassed acetonitrile (40 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (20 mL). The filtrate was concentrated under vacuo to yield a residue, which was purified by column chromatography on silica gel to obtain the pure product DMPz-Ph-I in 40% yield. $^1$H NMR ($CDCl_3$): δ2.30 (s, 3H), 2.32 (s, 3H), 6.00 (s, 1H), 7.22 (dd, 1H), 7.40 (d, 2H), 7.67 (d, 2H), 7.84 (s, 1H).

Synthesis of DMPz-Ph-Py

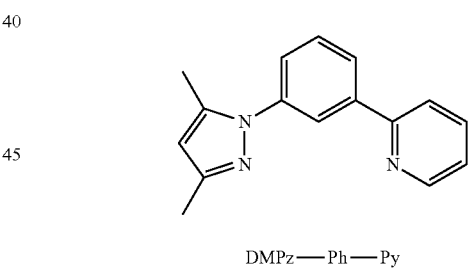

DMPz—Ph—Py

A mixture of DMPz-Ph-I (0.9 g, 3.0 mmol), (2-pyridyl)tri-n-butylstannane (4.5 mmol), $Pd(PPh_3)_2Cl_2$ (10 mg, 0.02 mmol), and LiCl (0.52 g, 12 mmol) in toluene (40 mL) was heated under reflux conditions for 3 days. After cooling to room temperature, the solid residue was filtered off, and water (50 mL) and $CH_2Cl_2$ (40 mL) were added to the filtrate. The organic phase was separated and dried ($MgSO_4$), and the solvent was evaporated. The crude product was purified by chromatograph (silica gel; hexanes-$Et_2O$, 4:1) to give ligand DMPz-Ph-Py as a light yellow liquid (70%). $^1$H NMR (500 MHz, $CDCl_3$): δ 2.32 (s, 3H), 2.35 (s, 3H), 6.01 (s, 1H), 7.46-7.49 (m, 1H), 7.55 (dd, 1H), 7.76-7.77 (m, 2H), 8.01 (m, 2H), 8.07 (dd, 1H), 8.70 (d, 1H).

Synthesis of DMPz-Ph-Py-PtCl

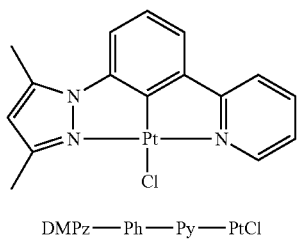

DMPz—Ph—Py—PtCl

Acetic acid (3.0 mL) and water (0.3 mL) were added to a mixture of DMPz-Ph-Py (typically 1.0 mmol) and $K_2PtCl_4$ (1 equiv) in a PYREX® vessel with a magnetic stir bar. The vessel was capped, and the mixture was heated under microwave irradiation for 30 minutes. Upon cooling to room temperature, a yellow-orange precipitate was formed. The precipitate was separated off from the yellow solution, washed sequentially with methanol, water, ethanol, and diethyl ether (typically 3×5 mL of each), and dried under vacuum. The product was purified by recrystallization from dimethyl sulfoxide/methanol.

Figure 12:
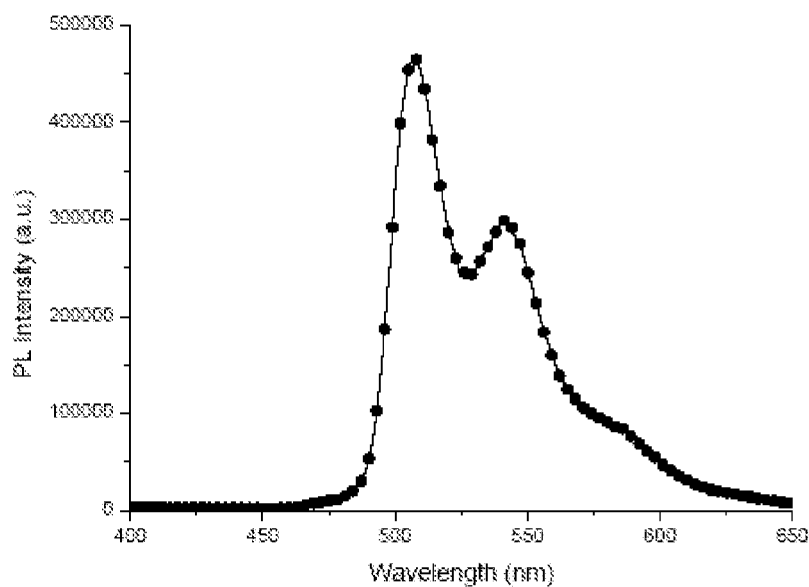
FIG. 12 is a photoluminescence spectrum of DMPz-Ph-Py-PtCl in dichloromethane.

FIG. 12 is a photoluminescence spectrum of DMPz-Ph-Py-PtCl in dichloromethane (DCM).

Synthesis of DMPz-Ph-MIz-PtCl

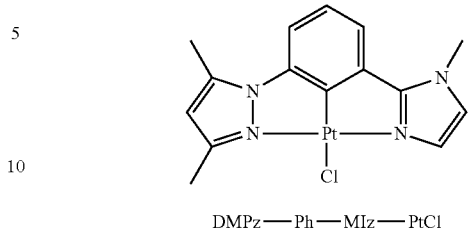

DMPz—Ph—MIz—PtCl

Acetic acid (3.0 mL) and water (0.3 mL) were added to a mixture of DMPz-Ph-MIz (typically 1.0 mmol) and $K_2PtCl_4$ (1 equiv) in a PYREX® vessel with a magnetic stir bar. The vessel was capped, and then the mixture was heated under microwave irradiation for 30 minutes. Upon cooling to room temperature, a yellow-orange precipitate was formed. The precipitate was separated off from the yellow solution, washed sequentially with methanol, water, ethanol, and diethyl ether (typically 3×5 mL of each), and dried under vacuum. The product was purified by recrystallization from dimethyl sulfoxide/methanol. $^1$H NMR (500 MHz, CDCl$_3$): δ 2.72 (s, 3H), 2.73 (s, 3H), 4.05 (s, 3H), 6.08 (s, 1H), 6.93 (d, 1H), 7.13-7.17 (m, 3H), 7.45 (dd, 1H).

Figure 13:
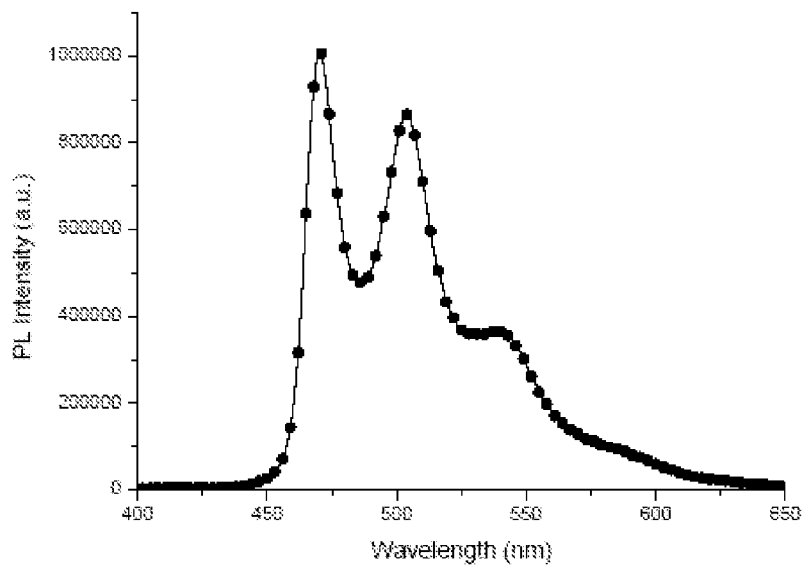
FIG. 13 is a photoluminescence spectrum of DMPz-Ph-MIz-PtCl in dichloromethane.

FIG. 13 is a photoluminescence spectrum of DMPz-Ph-MIz-PtCl in DCM.

Example 2

Synthesis of DMPz-Ph-MIz-PtCl

Synthesis of DMPz-Ph-MIz

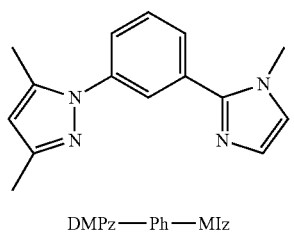

DMPz—Ph—MIz

A mixture of DMPz-Ph-I (0.9 g, 3.0 mmol), 1-methylimidazole (4.5 mmol), Pd(OAc)$_2$ (5 mg, 0.01 mmol), and CuI (1.2 g, 6.1 mmol) in degassed DMF (12 mL) was placed in a PYREX® vessel with a magnetic stir bar. The vessel was capped, and then the mixture was heated under microwave irradiation for 60 minutes. After cooling to room temperature, the mixture was poured into NH$_3$ solution (10%, 50 mL), and CH$_2$Cl$_2$ (40×3 mL) was added. The organic phase was separated and dried (MgSO$_4$), and the solvent was evaporated. The crude product was purified by chromatograph (silica gel; hexanes-Et$_2$O, 4:1) to give ligand DMPz-Ph-MIz as a light yellow liquid (80%). $^1$H NMR (500 MHz, CDCl$_3$): δ 2.29 (s, 3H), 2.34 (s, 3H), 3.77 (s, 3H), 6.00 (s, 1H), 6.99 (d, 1H), 7.14 (d, 1H), 7.49 (d, 1H), 7.53 (dd, 1H), 7.62 (d, 1H), 7.70 (s, 1H).

Example 3

Synthesis of DMPz-Ph-MIzCb-PtCl

Synthesis of DMPz-Ph-Iz

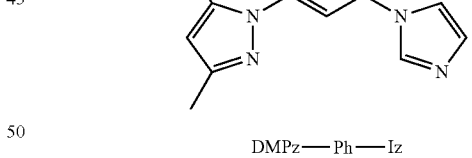

DMPz—Ph—Iz

After standard cycles of evacuation and back-fill with dry and pure nitrogen, an oven-dried Schlenk flask equipped with a magnetic stir bar was charged with Cu$_2$O (0.1 mmol, 10 mol %), syn-2-pyridinealdoxime (0.4 mmol, 20 mol %), 3,5-dimethylpyrazole (1.1 mmol), Cs$_2$CO$_3$ (2.5 mmol), and DMPz-Ph-I (1.0 mmol), and anhydrous and degassed acetonitrile (40 mL). The flask was stirred in an oil bath, and refluxed for 2 days. The reaction mixture was allowed to cool to room temperature, diluted with dichloromethane, and filtered through a plug of CELITE®, the filter cake being further washed with dichloromethane (20 mL). The filtrate was concentrated under vacuo to yield a residue, which was purified by column chromatography on silica gel to obtain the pure product DMPz-Ph-Iz.

Synthesis of DMPz-Ph-IMIz

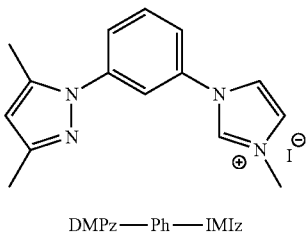

DMPz—Ph—IMIz

Methyl iodide (3 equiv) was syringed into a 50 mL round-bottomed flask charged with DMPz-Ph-Iz (1.0 mmol) and toluene (20 mL). The reaction was stirred under nitrogen in room temperature for 48 h. Pale-yellow precipitate was formed. The precipitate was filtered, washed with toluene, washed with ether, and air-dried to obtain DMPz-Ph-IMIz in 80% yield. $^1$H NMR (500 MHz, CDCl$_3$): δ 2.20 (s, 3H), 2.39 (s, 1H), 3.95 (s, 3H), 6.16 (s, 1H), 7.72-7.80 (m, 3H), 7.94 (d, 1H), 7.96 (d, 1H), 8.36 (dd, 1H), 9.82 (s, 1H).

Synthesis of DMPz-Ph-MIzCb-PtCl

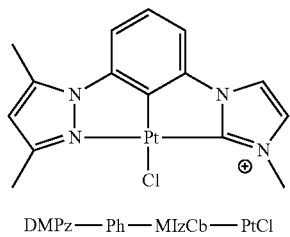

DMPz—Ph—MIzCb—PtCl

A mixture of DMPz-Ph-IMIz (1 mmol), K$_2$PtCl$_4$ (0.41 mg, 1 mmol), and DMSO (35 mL) was refluxed for 1 day. The mixture was allowed to cool to room temperature. Ether was added, the resulting yellow complex was filtered off and washed with MeOH, H$_2$O, EtOH, and Et$_2$O, and dried under vacuum to produce DMPz-Ph-MIzCb-PtCl in 80% yield. The product was purified by recrystallization from dimethyl sulfoxide/methanol for further testing.

Figure 14:
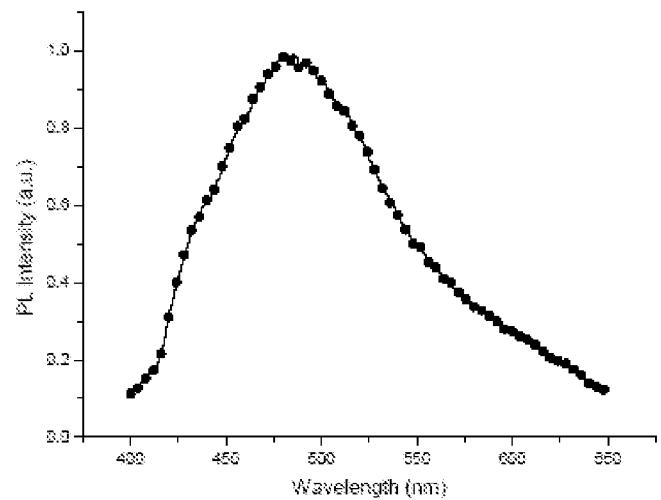
FIG. 14 is a photoluminescence spectrum of DMPz-Ph-MIzCb-PtCl in dichloromethane.

FIG. 14 is a photoluminescence spectrum of DMPz-Ph-MIzCb-PtCl in dichloromethane.

Example 4

Synthesis of DMPz-Py-MIz-PtCl

Synthesis of DMPz-Py-Br

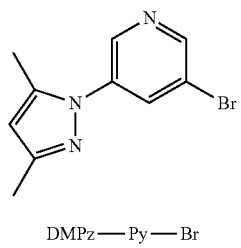

DMPz—Py—Br

After standard cycles of evacuation and back-fill with dry and pure nitrogen, an oven-dried Schlenk flask equipped with a magnetic stir bar was charged with Cu$_2$O (0.1 mmol, 10 mol %), syn-2-pyridinealdoxime (0.4 mmol, 20 mol %), 3,5-dimethylpyrazole (1.0 mmol), Cs$_2$CO$_3$ (2.5 mmol), 3,5-dibromopyridine (1.2 mmol), and anhydrous and degassed acetonitrile (40 mL). The flask was stirred in an oil bath, and refluxed for 3 days. The reaction mixture was allowed to cool to room temperature, diluted with dichloromethane and filtered through a plug of CELITE®, the filter cake being further washed with dichloromethane (20 mL). The filtrate was concentrated under vacuo to yield a residue, which was purified by column chromatography on silica gel to obtain the pure product DMPz-Py-Br in 60% yield. $^1$H NMR (CDCl$_3$): δ 2.31 (s, 3H), 2.35 (s, 3H), 6.05 (s, 1H), 741 (dd, 1H), 7.83 (d, 1H), 8.59 (d, 1H), 8.75 (d, 1H).

Synthesis of DMPz-Py-MIz

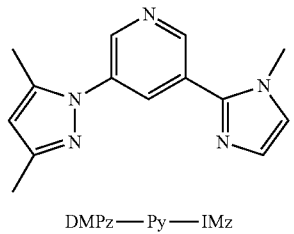

DMPz—Py—IMz

A mixture of DMPz-Py-Br (0.75 g, 3.0 mmol), 1-methylimidazole (4.5 mmol), Pd(OAc)$_2$ (5 mg, 0.01 mmol), KI (1.0 g, 6 mmol), and CuI (1.2 g, 6.1 mmol) in degassed DMF (12 mL) was heated under Ar at 140° C. for 4 days. After cooling to room temperature, the mixture was poured into NH$_3$ solution (10%, 50 mL), and CH$_2$Cl$_2$ (40×3 mL) was added. The organic phase was separated and dried (MgSO$_4$), and the solvent was evaporated. The crude product was purified by chromatograph (silica gel; ethyl acetate/methanol, 4:1) to give ligand DMPz-Py-MIz as a light yellow liquid (60%).

Synthesis of DMPz-Py-MIz-PtCl

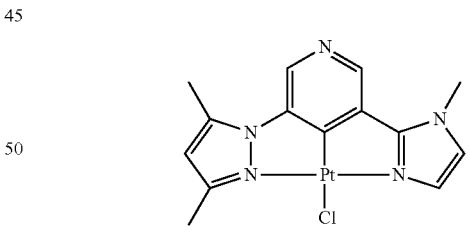

DMPz—Py—MIz—PtCl

A mixture of DMPz-Py-MIz (1 mmol), K$_2$PtCl$_4$ (0.41 mg, 1 mmol), and acetic acid (35 mL) was refluxed for 3 days. The mixture was allowed to cool to room temperature. The resulting yellow complex was filtered off and washed with MeOH, H$_2$O, EtOH, and Et$_2$O, and dried under vacuum to produce DMPz-Ph-MIz-PtCl in 70% yield. The product was purified by recrystallization from dimethyl sulfoxide/methanol for further testing.

Example 5

Synthesis of DMPz-Ph-MIzCb-PtCl

Synthesis of DMPz-Py-Iz

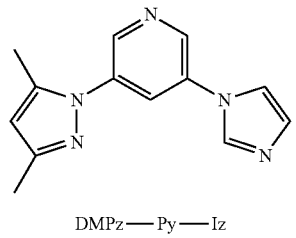

DMPz—Py—Iz

After standard cycles of evacuation and back-fill with dry and pure nitrogen, an oven-dried Schlenk flask equipped with a magnetic stir bar was charged with $Cu_2O$ (0.1 mmol, 10 mol %), syn-2-pyridinealdoxime (0.4 mmol, 20 mol %), 3,5-dimethylpyrazole (1.1 mmol), $Cs_2CO_3$ (2.5 mmol), DMPz-Py-Br (1.0 mmol), and anhydrous and degassed acetonitrile (40 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (20 mL). The filtrate was concentrated under vacuo to yield a residue, which was purified by column chromatography on silica gel to obtain the pure product DMPz-Py-Iz.

Synthesis of DMPz-Ph-IMIz

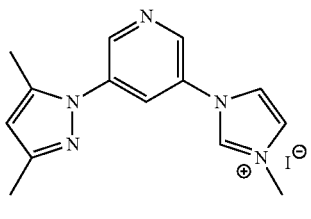

DMPz—Py—IMIz

Methyl iodide (3 equiv) was syringed into a 50 mL round-bottomed flask charged with DMPz-Py-Iz (1.0 mmol) and toluene (20 mL). The reaction was stirred under nitrogen in room temperature for 48 h. Pale-yellow precipitate was formed. The precipitate was filtered, washed with toluene, washed with ether, and air-dried to obtain DMPz-Py-IMIz in 75% yield.

Synthesis of DMPz-Ph-MIzCb-PtCl

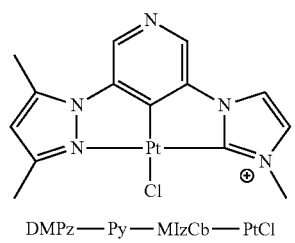

DMPz—Py—MIzCb—PtCl

A mixture of DMPz-Py-IMIz (1 mmol), $K_2PtCl_4$ (0.41 mg, 1 mmol), and DMSO (10 mL) was refluxed for 1 day. The mixture was allowed to cool to room temperature. Ether was added, the resulting yellow complex was filtered off and washed with MeOH, $H_2O$, EtOH, and $Et_2O$, and dried under vacuum to produce DMPz-Py-MIzCb-PtCl in 70% yield. The product was purified by recrystallization from dimethyl sulfoxide/methanol for further testing.

Example 6

Synthesis of DMPz-DFPh-Py-PtCl

Synthesis of DMPz-DFPh-Br

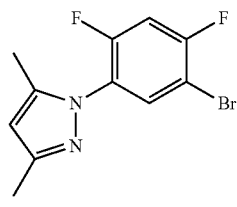

DMPz—DFPh—Br

After standard cycles of evacuation and back-fill with dry and pure nitrogen, an oven-dried Schlenk flask equipped with a magnetic stir bar was charged with $Cu_2O$ (0.1 mmol, 10 mol %), syn-2-pyridinealdoxime (0.4 mmol, 20 mol %), 3,5-dimethylpyrazole (1.1 mmol), $Cs_2CO_3$ (2.5 mmol), and 2,4-difluoro-5-iodo-bromobenzene (1.0 mmol), and anhydrous and degassed acetonitrile (40 mL). The flask was stirred in an oil bath, and refluxed for 4 days. The reaction mixture was allowed to cool to room temperature, diluted with dichloromethane and filtered through a plug of CELITE®, the filter cake being further washed with dichloromethane (20 mL). The filtrate was concentrated under vacuo to yield a residue, which was purified by column chromatography on silica gel to obtain the pure product DMPz-Ph-Br in 70% yield.

Synthesis of DMPz-DFPh-Py

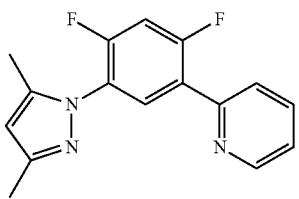

DMPz—DFPh—Py

A mixture of DMPz-DFPh-Br (3.0 mmol), (2-pyridyl)tri-n-butylstannane (4.5 mmol), $Pd(PPh_3)_2Cl_2$ (10 mg, 0.02 mmol), and LiCl (0.52 g, 12 mmol) in toluene (40 mL) was heated under reflux conditions for 3 days. After cooling to room temperature, the solid residue was filtered off, water (50 mL) and $CH_2Cl_2$ (40 mL) was added to the filtrate. The organic phase was separated and dried ($MgSO_4$), and the solvent was evaporated. The crude product was purified by chromatograph (silica gel; hexanes-$Et_2O$, 4:1) to give ligand DMPz-DFPh-Py as a light yellow liquid (60%).

Synthesis of DMPz-DFPh-Py-PtCl

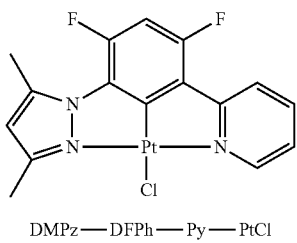

DMPz—DFPh—Py—PtCl

Acetic acid (3.0 mL) and water (0.3 mL) were added to a mixture of DMPz-DFPh-Py (typically 1.0 mmol) and $K_2PtCl_4$ (1 equiv) in a PYREX® vessel with a magnetic stir bar. The vessel was capped, and then the mixture was heated under microwave irradiation for 30 minutes. Upon cooling to room temperature, a yellow-orange precipitate was formed. The precipitate was separated off from the yellow solution, washed sequentially with methanol, water, ethanol, and diethyl ether (typically 3×5 mL of each), and dried under vacuum. The product was purified by recrystallization from dimethyl sulfoxide/methanol.

Example 7

Synthesis of DMPz-DFPh-MIz-PtCl

Synthesis of DMPz-DFPh-MIz

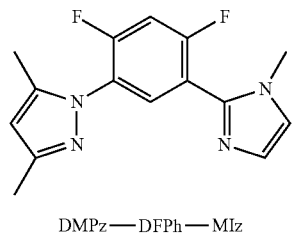

DMPz—DFPh—MIz

A mixture of DMPz-DFPh-Br (3.0 mmol), 1-methylimidazole (4.5 mmol), Pd(OAc)$_2$ (5 mg, 0.01 mmol), KI (1.0 g, 6 mmol), and CuI (1.2 g, 6.1 mmol) in degassed DMF (12 mL) was heated under Ar at 140° C. for 5 days. After cooling to room temperature, the mixture was poured into $NH_3$ solution (10%, 50 mL), and $CH_2Cl_2$ (40×3 mL) was added. The organic phase was separated and dried (MgSO$_4$), and the solvent was evaporated. The crude product was purified by chromatograph (silica gel; hexanes-Et$_2$O, 4:1) to give ligand DMPz-DFPh-MIz as a light yellow liquid (50%).

Synthesis of DMPz-DFPh-MIz-PtCl

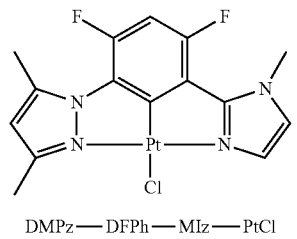

DMPz—DFPh—MIz—PtCl

Acetic acid (3.0 mL) and water (0.3 mL) were added to a mixture of DMPz-DFPh-MIz (typically 1.0 mmol) and $K_2PtCl_4$ (1 equiv) in a PYREX® vessel with a magnetic stir bar. The vessel was capped, and then the mixture was heated under microwave irradiation for 30 minutes. Upon cooling to room temperature, a yellow-orange precipitate was formed. The precipitate was separated off from the yellow solution, washed sequentially with methanol, water, ethanol, and diethyl ether (typically 3×5 mL of each), and dried under vacuum. The product was purified by recrystallization from dimethyl sulfoxide/methanol.

Example 8

Synthesis of DMPz-DFPh-MIzCb-PtCl

Synthesis of DMPz-DFPh-Iz

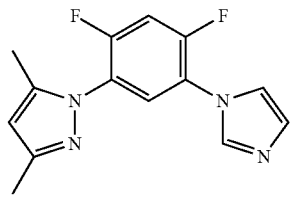

DMPz—DFPh—Iz

After standard cycles of evacuation and back-fill with dry and pure nitrogen, an oven-dried Schlenk flask equipped with a magnetic stir bar was charged with Cu$_2$O (0.1 mmol, 10 mol %), syn-2-pyridinealdoxime (0.4 mmol, 20 mol %), 3,5-dimethylpyrazole (1.1 mmol), Cs$_2$CO$_3$ (2.5 mmol), DMPz-DFPh-Br (1.0 mmol), and anhydrous and degassed acetonitrile (40 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (20 mL). The filtrate was concentrated under vacuo to yield a residue, which was purified by column chromatography on silica gel to obtain the pure product DMPz-DFPh-Iz.

Synthesis of DMPz-DFPh-IMIz

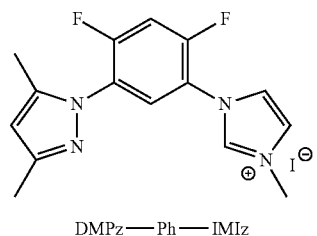

DMPz—Ph—IMIz

Methyl iodide (3 equiv) was syringed into a 50 mL round-bottomed flask charged with DMPz-DFPh-Iz (1.0 mmol) and toluene (20 mL). The reaction was stirred under nitrogen in room temperature for 48 h. Pale-yellow precipitate was formed. The precipitate was filtered, washed with toluene, washed with ether, and air-dried to obtain DMPz-DFPh-IMIz in 60% yield.

Synthesis of DMPz-DFPh-MIzCb-PtCl

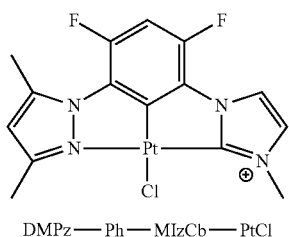

DMPz—Ph—MIzCb—PtCl

A mixture of DMPz-DFPh-IMIz (1 mmol), K₂PtCl₄ (0.41 mg, 1 mmol), and DMSO (35 mL) was refluxed for 1 day. The mixture was allowed to cool to room temperature. Ether was added, the resulting yellow complex was filtered off and washed with MeOH, H₂O, EtOH, and Et₂O, and dried under vacuum to produce DMPz-DFPh-MIzCb-PtCl in 70% yield. The product was purified by recrystallization from dimethyl sulfoxide/methanol for further testing.

Example 9

Synthesis of DMPz-DFPh-MIz-PtOPh and DMPz-DFPh-MIz-PtOPhBu

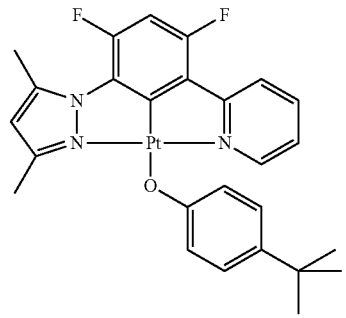

DMPz—DFPh—MIz—PtOPh

DMPz—DFPh—MIz—PtOPhBu

DMPz-DFPh-MIz-PtOPh and DMPz-DFPh-MIz-PtOPhBu were synthesized by the same procedure as Example 11, using DMPz-DFPh-MIz-PtCl as the starting material.

Example 10

Synthesis of DMPz-DFPh-Py-PtOPh and DMPz-DFPh-Py-PtOPhBu

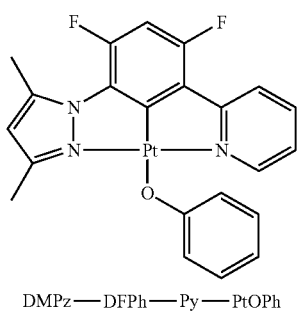

DMPz—DFPh—Py—PtOPh

DMPz—DFPh—Py—PtOPhBu

DMPz-DFPh-Py-PtOPh and DMPz-DFPh-Py-PtOPhBu were synthesized by the same procedure as Example 11, using DMPz-DFPh-Py-PtCl as the starting material.

Example 11

Synthesis of DMPz-Py-MIz-PtOPh and DMPz-Py-MIz-PtOPhBu

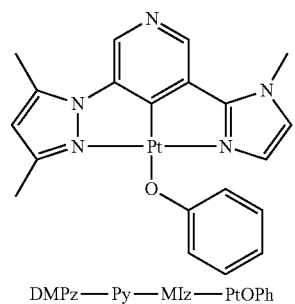

DMPz—Py—MIz—PtOPh

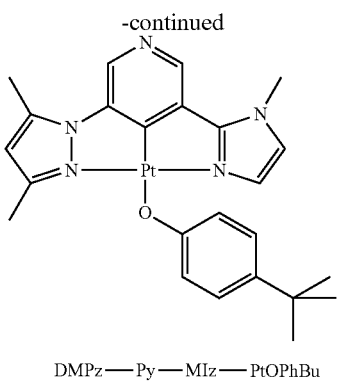

DMPz—Py—MIz—PtOPhBu

DMPz-Py-MIz-PtOPh, and DMPz-Py-MIz-PtOPhBu were synthesized by the same procedure as Example 11, using DMPz-Py-MIz-PtCl as the starting material.

Example 12

Synthesis of DMPz-Ph-MIz-PtOPh and DMPz-Ph-MIz-PtOPhBu

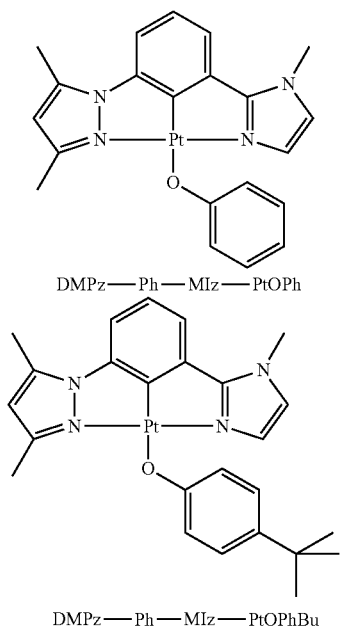

DMPz—Ph—MIz—PtOPh

DMPz—Ph—MIz—PtOPhBu

DMPz-Ph-MIz-PtOPh and DMPz-Ph-MIz-PtOPhBu were synthesized by the same procedure as Example 11, using DMPz-Ph-MIz-PtCl as the starting material. DMPz-Ph-MIz-PtOPhBu: $^1$H NMR (CDCl$_3$): δ 1.27 (s, 9H), 2.55 (s, 3H), 2.71 (s, 3H), 4.00 (s, 3H), 6.04 (s, 1H), 6.77 (dd, 2H), 7.01 (d, 2H), 7.09-7.15 (m, 5H).

Figure 15:
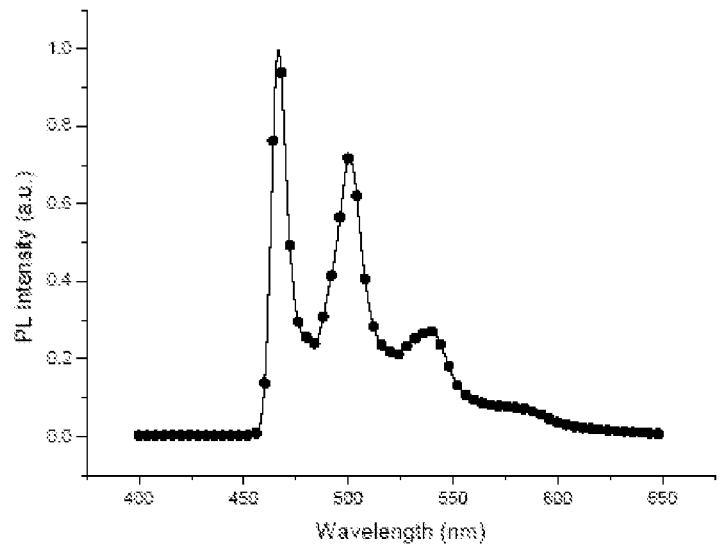
FIG. 15 is a photoluminescence spectrum of DMPz-Ph-MIz-PtOPhBu in dichloromethane.

FIG. 15 is a photoluminescence spectrum of DMPz-Ph-MIz-PtOPhBu in DCM.

Example 13

Synthesis of Ph-Py-Pz-PtCl

Synthesis of Ph-Py-Br

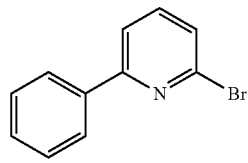

Ph—Py—Br

A mixture of 2,6-dibromopyridine (2.36 g, 10 mmol), phenylboronic acid (1.0 eq), Pd(OAc)$_2$ (0.05 equiv), and PPh$_3$ (0.2 equiv) were dissolved in dimethoxyethane/2M K$_2$CO$_3$ aqueous solution (80 mL, 1:1) under nitrogen atmosphere. The mixture was heated and refluxed for 24 h. After being cooled to room temperature, the reaction mixture was diluted with EtOAc, and poured into a brine solution. The organic layer was separated, washed with the water, dried, and filtered, and the filtrate was concentrated under reduced pressure. The residue was purified by column chromatography on silica gel to obtain the pure product Ph-Py-Br in 74% yield. $^1$H NMR (CDCl$_3$): δ 7.41-7.51 (m, 4H), 7.60 (dd, 1H), 7.70 (dd, 1H), 8.00 (dd, 2H).

Synthesis of Ph-Py-Pz

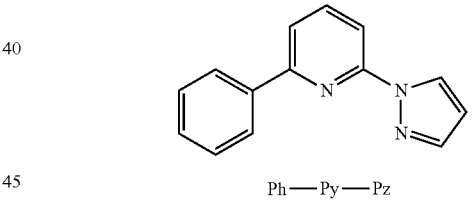

Ph—Py—Pz

After standard cycles of evacuation and back-fill with dry and pure nitrogen, an oven-dried Schlenk flask equipped with a magnetic stir bar was charged with Cu$_2$O (0.1 mmol, 10 mol %), syn-2-pyridinealdoxime (0.4 mmol, 20 mol %), pyrazole (1.2 mmol), Cs$_2$CO$_3$ (2.5 mmol), Ph-Py-Br (1.0 mmol), and anhydrous and degassed acetonitrile (40 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (20 mL). The filtrate was concentrated under vacuo to yield a residue, which was purified by column chromatography on silica gel to obtain the pure product Ph-Py-Pz in 80% yield. $^1$H NMR (CDCl$_3$): δ 6.50 (dd, 1H), 7.46 (dd, 1H), 7.52 (dd, 2H), 7.65 (d, 1H), 7.77 (d, 1h), 7.89 (d, 1H), 7.94 (d, 1H), 8.09 (d, 2H), 8.76 (d, 1H).

Synthesis of Ph-Py-Pz-PtCl

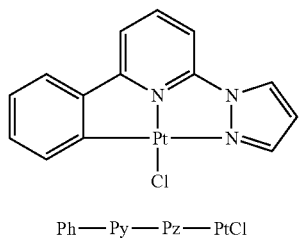

Ph—Py—Pz—PtCl

Acetic acid (3.0 mL) and water (0.3 mL) were added to a mixture of Ph-Py-Pz (typically 1.0 mmol) and $K_2PtCl_4$ (1 equiv) in a PYREX® vessel with a magnetic stir bar. The vessel was capped, and the mixture was heated under microwave irradiation for 30 minutes. Upon cooling to room temperature, a yellow-orange precipitate was formed. The precipitate was separated from the yellow solution, washed sequentially with methanol, water, ethanol, and diethyl ether (typically 3×5 mL of each), and dried under vacuum. The product was purified by recrystallization from dimethyl sulfoxide/methanol for further testing. $^1$H NMR (500 MHz, $CDCl_3$): δ 6.77 (dd, 1H), 7.11 (dd, 1H), 7.15 (d, 1H), 7.26 (dd, 1H), 7.31 (d, 1H), 7.72 (d, 1H), 7.80 (dd, 1H), 7.86 (d, 1H), 8.14 (d, 1H).

Figure 16:
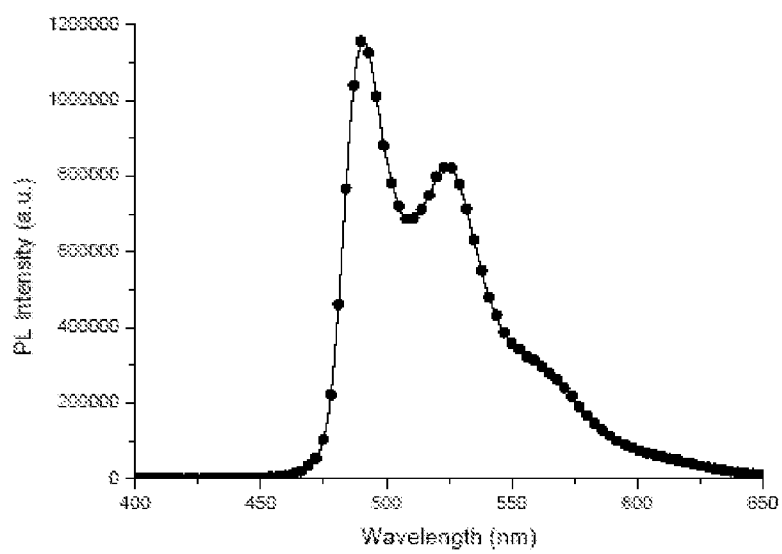
FIG. 16 is a photoluminescence spectrum of Ph-Py-Pz-PtCl in dichloromethane.

FIG. 16 is a photoluminescence spectrum of Ph-Py-Pz-PtCl in DCM.

Example 14

Synthesis of Ph-Py-MIzCb-PtCl

Synthesis of Ph-Py-Iz

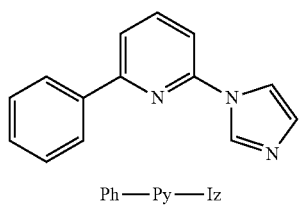

Ph—Py—Iz

After standard cycles of evacuation and back-fill with dry and pure nitrogen, an oven-dried Schlenk flask equipped with a magnetic stir bar was charged with $Cu_2O$ (0.1 mmol, 10 mol %), syn-2-pyridinealdoxime (0.4 mmol, 20 mol %), imidazole (1.2 mmol), $Cs_2CO_3$ (2.5 mmol), Ph-Py-Br (1.0 mmol), and anhydrous and degassed acetonitrile (40 mL). The flask was stirred in an oil bath, and refluxed for 2 days. The reaction mixture was allowed to cool to room temperature, diluted with dichloromethane, and filtered through a plug of CELITE®, the filter cake being further washed with dichloromethane (20 mL). The filtrate was concentrated under vacuo to yield a residue, which was purified by column chromatography on silica gel to obtain the pure product Ph-Py-Iz in 75% yield. $^1$H NMR ($CDCl_3$): δ 7.24 (d, 1H), 7.29 (d, 1H), 7.49 (dd, 1H), 7.52 (dd, 2H), 7.70 (d, 1H), 7.76 (d, 1H), 7.90 (dd, 1H), 8.09 (d, 2H), 8.48 (s, 1H).

Synthesis of Ph-Py-Iz

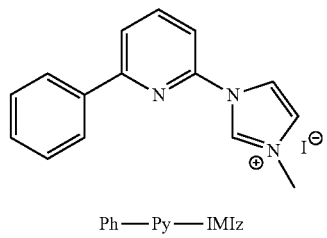

Ph—Py—IMIz

Methyl iodide (3 equiv) was syringed into a 50 mL round-bottomed flask charged with Ph-Py-Iz (10 mmol) and toluene (30 mL). The reaction was stirred under nitrogen in room temperature for 48 h. Pale-yellow precipitate was formed. The precipitate was filtered, washed with toluene, washed with ether, and air-dried to obtain Ph-Py-Iz in 90% yield. $^1$H NMR (DMSO): δ 3.97 (s, 3H), 7.51-7.55 (m, 3H), 7.91 (d, 1H), 7.96 (d, 1H), 8.19 (d, 1H), 8.23-8.26 (m, 3H), 8.60 (d, 1H), 10.14 (s, 1H).

Synthesis of Ph-Py-MIzCb-PtCl

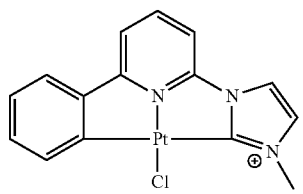

Ph—Py—MIzCb—PtCl

A mixture of Ph-Py-IMIz (1 mmol), $K_2PtCl_4$ (0.41 mg, 1 mmol), and acetic acid (35 mL) was refluxed for 3 days. The mixture was allowed to cool to room temperature. The resulting yellow complex was filtered off and washed with MeOH, $H_2O$, EtOH, and $Et_2O$, and dried under vacuum to produce Ph-Py-MIzCb-PtCl in 80% yield. The product was purified by recrystallization from dimethyl sulfoxide/methanol for further testing.

Example 15

Synthesis of Pz-Py-Iz-PtCl

Synthesis of Pz-Py-Br

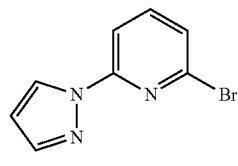

Pz—Py—Br

After standard cycles of evacuation and back-fill with dry and pure nitrogen, an oven-dried Schlenk flask equipped with a magnetic stir bar was charged with $Cu_2O$ (1 mmol, 10 mol %), syn-2-pyridinealdoxime (4 mmol, 20 mol %), pyrazole (12 mmol), $Cs_2CO_3$ (25 mmol), 2,6-dibromopyridine (10 mmol), and anhydrous and degassed acetonitrile (100 mL). The flask was stirred in an oil bath, and refluxed for 2 days. The reaction mixture was allowed to cool to room temperature, diluted with dichloromethane, and filtered through a plug of CELITE®, the filter cake being further washed with dichloromethane (100 mL). The filtrate was concentrated under vacuo to yield a residue, which was purified by column chromatography on silica gel to obtain the pure product Pz-Py-Br in 44% yield. $^1$H NMR (CDCl$_3$): δ 6.48 (dd, 1H), 7.36 (d, 1H), 7.67 (dd, 1H), 7.74 (d, 1H), 7.94 (d, 1H), 8.54 (d, 1H).

Synthesis of Pz-Py-Iz

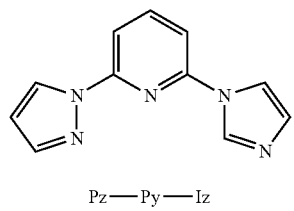

Pz—Py—Iz

After standard cycles of evacuation and back-fill with dry and pure nitrogen, an oven-dried Schlenk flask equipped with a magnetic stir bar was charged with Cu$_2$O (0.1 mmol, 10 mol %), syn-2-pyridinealdoxime (0.4 mmol, 20 mol %), pyrazole (1.2 mmol), Cs$_2$CO$_3$ (2.5 mmol), Pz-Py-Br (1.0 mmol), and anhydrous and degassed acetonitrile (40 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (30 mL). The filtrate was concentrated under vacuo to yield a residue, which was purified by column chromatography on silica gel to obtain the pure product Pz-Py-Iz in 85% yield. $^1$H NMR (CDCl$_3$): δ 6.49 (dd, 1H), 7.19-7.23 (m, 2H), 7.64 (d, 1H), 7.75 (d, 1H), 7.84-7.94 (m, 2H), 8.37 (s, 1H) 8.54 (d, 1H).

Synthesis of Pz-Py-Iz-PtCl

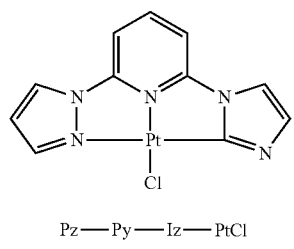

Pz—Py—Iz—PtCl

A mixture of Pz-Py-Iz (1 mmol), K$_2$PtCl$_4$ (0.41 mg, 1 mmol), and acetic acid (35 mL) was refluxed for 3 days. The mixture was allowed to cool to room temperature. The resulting orange complex was filtered off and washed with MeOH, H$_2$O, EtOH, and Et$_2$O, and dried under vacuum to produce Pz-Py-Iz-PtCl in 75% yield. The product was purified by recrystallization from dimethyl sulfoxide/methanol for further testing.

Example 16

Synthesis of DMPz-Py-Iz-PtCl

Synthesis of DMPz-Py-Br

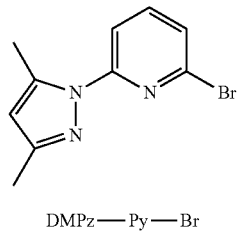

DMPz—Py—Br

After standard cycles of evacuation and back-fill with dry and pure nitrogen, an oven-dried Schlenk flask equipped with a magnetic stir bar was charged with Cu$_2$O (1 mmol, 10 mol %), syn-2-pyridinealdoxime (4 mmol, 20 mol %), 3,5-dimethylpyrazole (12 mmol), Cs$_2$CO$_3$ (25 mmol), and 2,6-dibromopyridine (10 mmol), and anhydrous and degassed acetonitrile (100 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (100 mL). The filtrate was concentrated under vacuo to yield a residue, which was purified by column chromatography on silica gel to obtain the pure product DMPz-Py-Br in 44% yield. $^1$H NMR (CDCl$_3$, 500 MHz): δ 2.29 (s, 3H), 2.66 (s, 3H), 6.00 (s, 1H), 7.30 (d, 2H), 7.61 (dd, 1H), 7.85 (d, 1H).

Synthesis of DMPz-Py-Iz

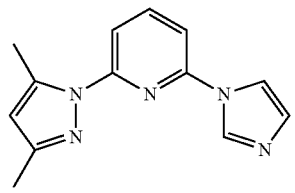

DMPz—Py—Iz

After standard cycles of evacuation and back-fill with dry and pure nitrogen, an oven-dried Schlenk flask equipped with a magnetic stir bar was charged with Cu$_2$O (0.1 mmol, 10 mol %), syn-2-pyridinealdoxime (0.4 mmol, 20 mol %), pyrazole (1.2 mmol), Cs$_2$CO$_3$ (2.5 mmol), DMPz-Py-Br (1.0 mmol), and anhydrous and degassed acetonitrile (40 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (30 mL). The filtrate was concentrated under vacuo to yield a residue, which was purified by column chromatography on silica gel to obtain the pure product DMPz-Py-Iz in 80% yield. $^1$H NMR (CDCl$_3$): δ 2.31 (s 3H), 2.74 (s, 3H), 6.05 (s, 1H), 7.17 (dd, 1H), 7.22 (s, 1H), 7.62 (s, 1H), 7.86-7.91 (m, 2H), 8.35 (s 1H).

Synthesis of DMPz-Py-Iz-PtCl

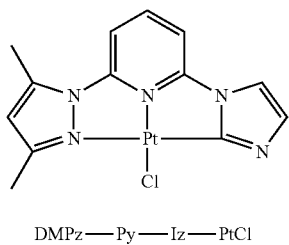

DMPz—Py—Iz—PtCl

A mixture of DMPz-Py-Iz (1 mmol), K$_2$PtCl$_4$ (0.41 mg, 1 mmol), and acetic acid (35 mL) was refluxed for 3 days. The mixture was allowed to cool to room temperature. The resulting orange complex was filtered off and washed with MeOH, H$_2$O, EtOH, and Et$_2$O, and dried under vacuum to produce DMPz-Py-Iz-PtCl in 75% yield. The product was purified by recrystallization from dimethyl sulfoxide/methanol for further testing.

Example 17

Synthesis of Iz-Py-MIzCb-PtCl

Synthesis of DIz-Py

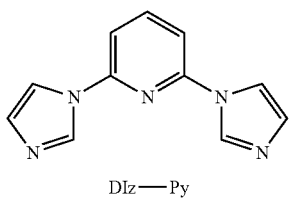

DIz—Py

After standard cycles of evacuation and back-fill with dry and pure nitrogen, an oven-dried Schlenk flask equipped with a magnetic stir bar was charged with Cu$_2$O (0.1 mmol, 10 mol %), syn-2-pyridinealdoxime (0.4 mmol, 20 mol %), imidazole (2.5 mmol), Cs$_2$CO$_3$ (5 mmol), and 2,6-dibromopyridine (1.0 mmol), and anhydrous and degassed acetonitrile (80 mL). The flask was stirred in an oil bath, and refluxed for 3 days. The reaction mixture was allowed to cool to room temperature, diluted with dichloromethane and filtered through a plug of CELITE®, the filter cake being further washed with dichloromethane (60 mL). The filtrate was concentrated under vacuo to yield a residue, which was purified by column chromatography on silica gel to obtain the pure product DIz-Py in 78% yield. $^1$H NMR (CDCl$_3$): δ 7.23 (s, 2H), 7.29 (d, 2H), 7.67 (s, 2H), 7.07 (t, 2H), 8.38 (s, 2H).

Synthesis of Iz-Py-IMIz

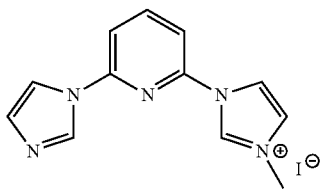 [SMILES: C[n+]1ccn(-c2cccc(-n3ccnc3)n2)c1 ; [I-]]

Methyl iodide (5 equiv) was syringed into a 50 mL round-bottomed flask charged with DIz-Py (10 mmol) and toluene (40 mL). The reaction was stirred under nitrogen in room temperature for 96 h. Pale-yellow precipitate was formed. The precipitate was filtered, washed with toluene, washed with ether, and air-dried to obtain Iz-Py-IMIz in 80% yield. $^1$H NMR (DMSO): δ 3.98 (s, 3H), 7.20 (s, 1H), 7.92 (d, 1H), 7.96 (dd, 1H), 8.00 (d, 1H), 8.19 (s, 1H), 8.37 (dd, 1H), 8.64 (dd, 1H), 8.84 (s, 1H), 10.19 (s, 1H).

Synthesis of Iz-Py-MIzCb-PtCl

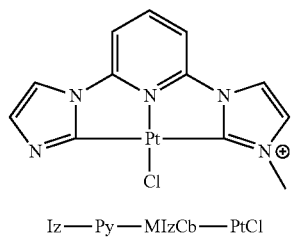

Iz—Py—MIzCb—PtCl

A mixture of Iz-Py-IMIz (1 mmol), K$_2$PtCl$_4$ (0.41 mg, 1 mmol), and DMSO (35 mL) was refluxed for 1 day. The mixture was allowed to cool to room temperature. Ether was added, the resulting yellow complex was filtered off and washed with MeOH, H$_2$O, EtOH, and Et$_2$O, and dried under vacuum to produce Iz-Py-MIzCb-PtCl in 73% yield. The product was purified by recrystallization from dimethyl sulfoxide/methanol for further testing.

Figure 17:
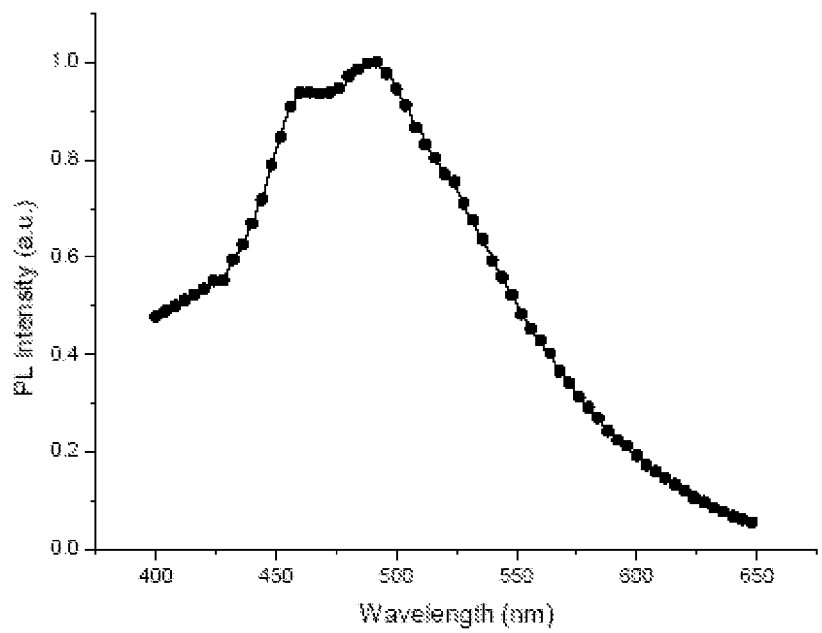
FIG. 17 is a photoluminescence spectrum of Iz-Py-MIzCb-PtCl in dichloromethane.

FIG. 17 is a photoluminescence spectrum of Iz-Py-MIzCb-PtCl in dichloromethane.

Example 18

Synthesis of MIz-Py-O-Ph-PtCl

Synthesis of MIz-Py-Br

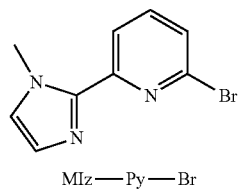

MIz—Py—Br

A 100 mL round bottom flask was brought into a nitrogen glovebox and charged with 2,6-dibromopyridine (10 mmol), 1-methylimidozole (10 mmol), Copper(I) iodide (20 mmol), palladium acetate (0.5 mmol, 5 mol %), and DMF (40 mL). A magnetic stir bar was added and the mixture bubbled for 30 minutes with nitrogen. The flask was then placed into a microwave under nitrogen, with a condenser attached. The mixture was irradiated under microwave at 180 W for 3 hours at 150° C. After cooling, the contents were placed into a stirring mixture of a 20% solution of NH$_4$OH and DCM. After 30 minutes, the contents were placed in a separatory funnel and the aqueous phase washed 3 times with DCM. The organic fractions were collected, washed once with water, and dried with MgSO$_4$. After filtering, the solution was reduced under vacuo. The residue was subjected to column chromatography with basic aluminum oxide and pure product was collected in 30% yield. $^1$H NMR (CDCl$_3$, 400 MHz): δ 4.12 (s, 3H), 6.98 (d, 1H), 7.12 (d, 1H), 7.39 (d, 1H), 7.60 (dd, 1H), 8.15 (d, 1H).

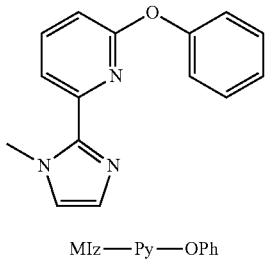

MIz—Py—OPh

Synthesis of MIz-Py-O-Ph

A 35 mL microwave flask was brought into a nitrogen glove box and charged with MIz-Py-Br (5 mmol), phenol (10 mmol), copper powder (1 mmol, 20 mol %), and cesium carbonate (15 mmol). 20 mL of DMF and a magnetic stir bar were added and the solution was bubbled with nitrogen for 30 minutes. The flask was then placed in the microwave and irradiated for 20 min, at 60 W, at 100 C. After cooling reaction contents were added to 150 mL of DCM and placed in a separatory funnel with a 35% solution of NaOH. Organic portion was then separated and washed with water. The organic portion was selected and dried with magnesium sulfate. After filtering the solution was reduced under vacuo and subjected to column chromatography on basic aluminum oxide to yield pure product with a 65% yield. $^1$H NMR (CDCl$_3$, 400 MHz): δ 3.52 (s, 3H), 6.81 (d, 1H), 6.89 (d, 1H), 7.04 (d, 1H), 7.15 (d, 2H), 7.20 (t, 1H), 7.39 (dd, 2H), 7.76 (dd, 1H), 7.89 (d, 1H).

Synthesis of MIz-Py-O-Ph-PtCl

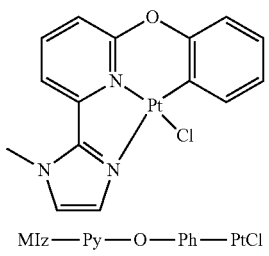

MIz—Py—O—Ph—PtCl

A 50 mL round bottom flask was charged with MIz-Py-O-Ph (2 mmol), K$_2$PtCl$_4$ (1.8 mmol), and acetic acid (20 mL). The vessel was placed in oil and refluxed for 2 days. The resulting solid was filtered and washed with water, followed by methanol, followed by ether and dried. The product was purified by recrystallization from dimethyl sulfoxide/methanol for further testing. $^1$H NMR (DMSO, 400 MHz): δ 4.166 (s, 3H), 6.93 (d, 1H), 7.05-7.13 (m, 2H), 7.46 (d, 1H), 7.53 (d, 1H), 7.81 (s, 1H), 7.92 (d, 1H), 8.30 (dd, 1H), 8.39 (dd, 1H).

Figure 18:
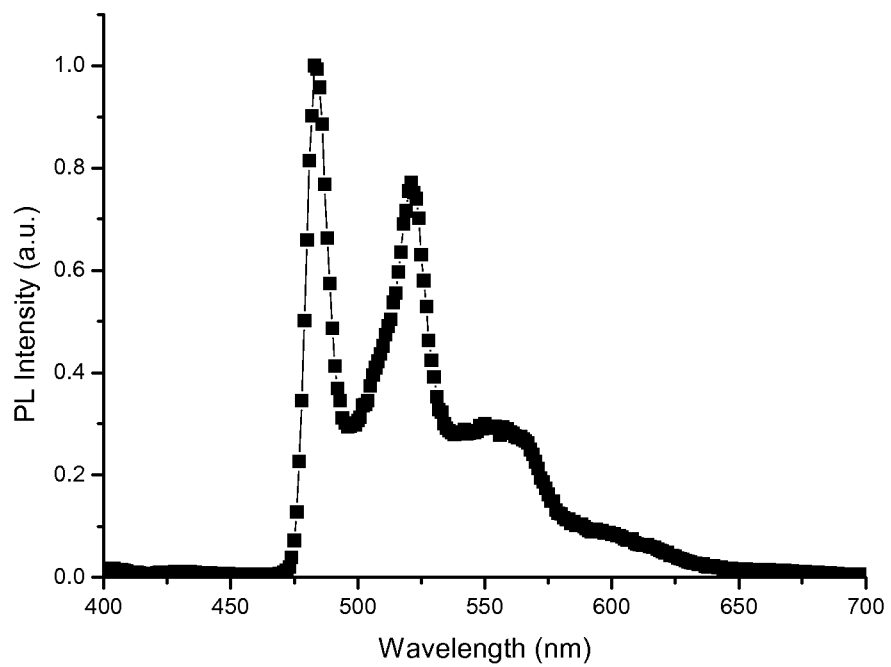
FIG. 18 is a photoluminescence spectrum of MIz-Py-O-Ph-PtCl in 2-methyltetrahydrofuran.

FIG. 18 is a photoluminescence spectrum of MIz-Py-O-Ph-PtCl in 2-methyltetrahydrofuran.

Example 19

Synthesis of DMPz-Py-O-Ph-PtCl

Synthesis of DMPz-Py-O-Ph

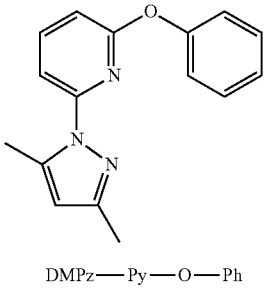

DMPz—Py—O—Ph

A 35 mL microwave flask was brought into a nitrogen glove box and charged with DMPz-Py-Br (5 mmol), phenol (10 mmol), copper powder (1 mmol, 20 mol %), and cesium carbonate (15 mmol). 20 mL of DMF and a magnetic stir bar were added and the solution was bubbled with nitrogen for 30 minutes. The flask was irradiated under microwave at 60 W and 100° C. for 20 min. After cooling reaction contents were added to 150 mL of DCM and placed in a separatory funnel with a 35% solution of NaOH. Organic portion was then separated and washed with water. The organic portion was selected and dried with magnesium sulfate. After filtering the solution was reduced under vacuo and subjected to column chromatography on silica to yield pure product with a 75% yield. $^1$H NMR (CDCl$_3$, 400 MHz): δ 2.06 (s, 3H), 2.24 (s, 3H), 5.84 (s, 1H), 6.76 (d, 1H), 7.13 (d, 2H), 7.20 (t, 1H), 7.38 (dd, 2H), 7.55 (d, 1H), 7.75 (dd, 1H).

Synthesis of DMPz-Py-O-Ph-PtCl

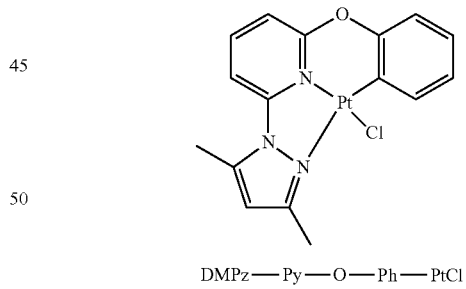

DMPz—Py—O—Ph—PtCl

A 50 mL round bottom flask was charged with DMPz-Py-O-Ph (2 mmol), K$_2$PtCl$_4$ (1.8 mmol), and acetic acid (20 mL). The vessel was placed in oil and refluxed for 2 days. The resulting solid was filtered and washed with water, followed by methanol, followed by ether and dried. The product was purified by recrystallization from dimethyl sulfoxide/methanol for further testing. $^1$H NMR (DMSO, 400 MHz): δ 2.65 (s, 3H), 2.74 (s, 3H), 6.61 (s, 1H), 6.9-6.95 (m, 2H), 7.04 (d, 1H), 7.05 (d, 1H), 7.35 (d, 1H), 7.67 (d, 1H), 8.15 (d, 1H), 8.33 (t, 1H).

Figure 19:
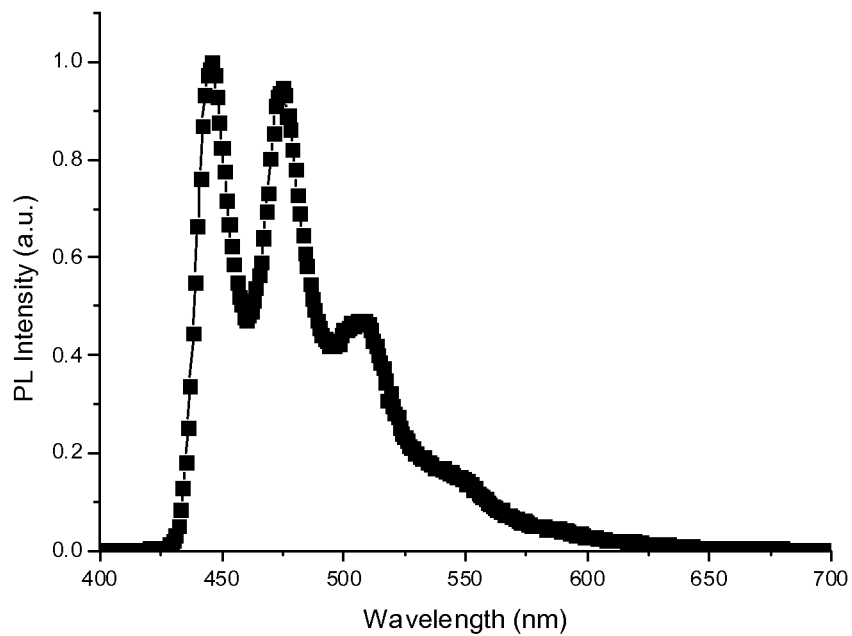
FIG. 19 is a photoluminescence spectrum of DMPz-Py-O-Ph-PtCl in 2-methyltetrahydrofuran.

FIG. 19 is a photoluminescence spectrum of DMPz-Py-O-Ph-PtCl in 2-methyltetrahydrofuran.

Example 20

Synthesis of DMPz-Ph-O-Py-PtCl

Synthesis of Py-O-Ph-I

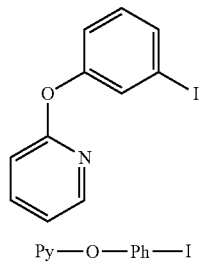

Py—O—Ph—I

A 35 mL microwave flask was brought into a nitrogen glove box and charged with 2-bromopyridine (10 mmol), 3-iodophenol (5 mmol), copper powder (1 mmol, 20 mol %), and cesium carbonate (15 mmol). 20 mL of DMF and a magnetic stir bar were added and the solution was bubbled with nitrogen for 30 minutes. The flask was irradiated under microwave at 60 W and 100° C. for 20 min. After cooling reaction contents were added to 150 mL of DCM and placed in a separatory funnel with a 35% solution of NaOH. Organic portion was then separated and washed with water. The organic portion was selected and dried with magnesium sulfate. After filtering the solution was reduced under vacuo and subjected to column chromatography on silica to yield pure product with a 45% yield.

Synthesis of DMPz-Ph-O-Py

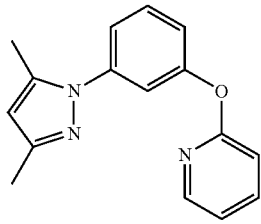

DMPz—Ph—O—Py

After standard cycles of evacuation and back-fill with dry and pure nitrogen, an oven-dried Schlenk flask equipped with a magnetic stir bar was charged with $Cu_2O$ (1 mmol, 10 mol %), syn-2-pyridinealdoxime (4 mmol, 20 mol %), 3,5-dimethylpyrazole (12 mmol), $Cs_2CO_3$ (25 mmol), and Py-O-Ph-I (10 mmol), and anhydrous and degassed acetonitrile (100 mL). The flask was stirred in an oil bath, and refluxed for 2 days. The reaction mixture was allowed to cool to room temperature, diluted with dichloromethane and filtered through a plug of CELITE®, the filter cake being further washed with dichloromethane (100 mL). The filtrate was concentrated under vacuo to yield a residue, which was purified by column chromatography on silica gel to obtain the pure product DMPz-Ph-O-Py in 70% yield. $^1$H NMR ($CDCl_3$, 400 MHz): δ 2.26 (s, 3H), 2.32 (s, 3H), 5.97 (s, 1H), 6.91 (d, 1H), 7.00 (d, 1H), 7.10 (dd, 1H), 7.23 (d, 1H), 7.26 (dd, 1H), 7.44 (dd, 1H), 7.68 (dd, 1H), 8.19 (dd, 1H).

Synthesis of DMPz-Ph-O-Py-PtCl

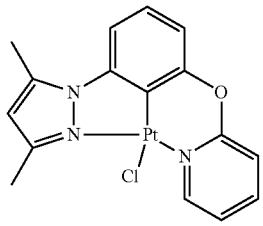

DMPz—Ph—O—Py—PtCl

A 50 mL round bottom flask was charged with DMPz-Ph-O-Py (2 mmol), $K_2PtCl_4$ (1.8 mmol), and acetic acid (20 mL). The vessel was placed in oil and refluxed for 2 days. The resulting solid was filtered and washed with water, followed by methanol, followed by ether and dried. The product was purified by recrystallization from dimethyl sulfoxide/methanol for further testing. $^1$H NMR ($d_6$-DMSO, 400 MHz): δ 2.69 (s, 3H), 2.74 (s, 3H), 6.37 (s, 1H), 6.94 (dd, 1H), 7.25-7.31 (m, 3H), 7.44 (dd, 1H), 8.17 (ddd, 1H), 10.04 (ddd, 1H).

Figure 20:
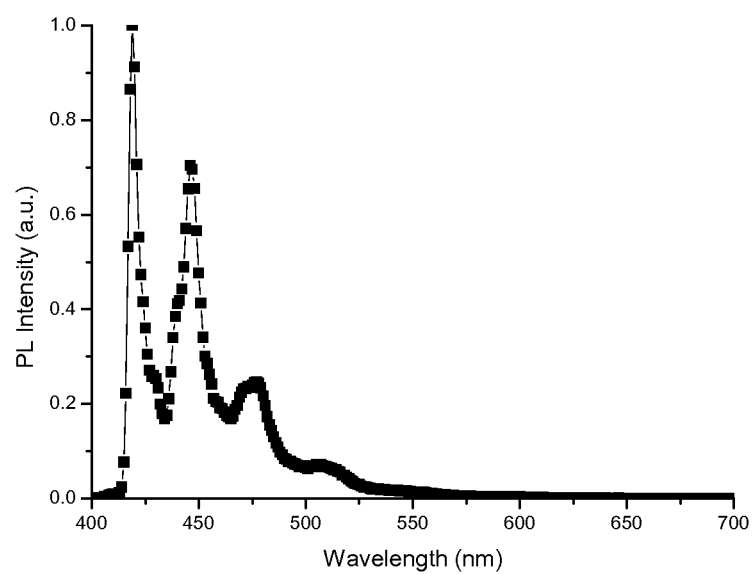
FIG. 20 is a photoluminescence spectrum of DMPz-Ph-O-Py-PtCl in 2-methyltetrahydrofuran.

FIG. 20 is a photoluminescence spectrum of DMPz-Ph-O-Py-PtCl in 2-methyltetrahydrofuran.

Example 21

Synthesis of MIz-Ph-O-Py-PtCl

Synthesis of MIz-Ph-O-Py

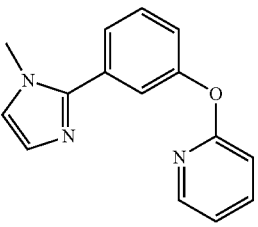

MIz—Ph—O—Py

A 100 mL round bottom flask was brought into a nitrogen glovebox and charged with Py-O-Ph-I (10 mmol), 1-methylimidozole (15 mmol), Copper(I) iodide (20 mmol), palladium acetate (0.5 mmol, 5 mol %), and DMF (40 mL). A magnetic stir bar was added and the mixture bubbled for 30 minutes with nitrogen. The flask was then placed into a microwave under nitrogen, with a condenser attached. The mixture was irradiated under microwave at 180 W for 3 hours at 150° C. After cooling, the contents were placed into a stirring mixture of a 20% solution of $NH_4OH$ and DCM. After 30 minutes, the contents were placed in a separatory funnel and the aqueous phase washed 3 times with DCM. The organic fractions were collected, washed once with water, and dried with $MgSO_4$. After filtering, the solution was reduced under vacuo. The residue was subjected to column chromatography with basic aluminum oxide and pure product was collected in 70% yield. $^1$H NMR ($CDCl_3$, 400 MHz): δ 3.78 (s, 3H), 6.94 (ddd, 1H), 6.96 (d, 1H), 7.00 (ddd, 1H), 7.11 (d, 1H), 7.20 (ddd, 1H), 7.42 (ddd, 1H), 7.47-7.49 (m, 2H). 7.69 (ddd, 1H), 8.20 (ddd, 1H).

Synthesis of MIz-Ph-O-Py-PtCl

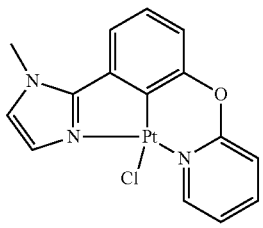

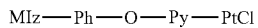

A 50 mL round bottom flask was charged with MIz-Ph-O-Py (2 mmol), $K_2PtCl_4$ (1.8 mmol), and acetic acid (20 mL). The vessel was placed in oil and refluxed for 2 days. The resulting solid was filtered and washed with water, followed by methanol, followed by ether and dried. The product was purified by recrystallization from dimethyl sulfoxide/methanol for further testing.

A number of embodiments of the invention have been described. Nevertheless, it will be understood that various modifications may be made without departing from the spirit and scope of the invention. Accordingly, other embodiments are within the scope of the following claims.

What is claimed is:

1. A platinum (II) complex of the formula,

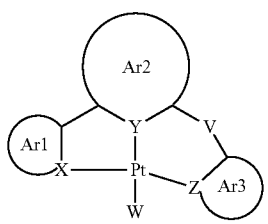

wherein:
Ar1 is a 1,2-diazole ring, Ar2 is a pyridine ring, and Ar3 is a phenyl ring, and Ar1, Ar2, and Ar3 together form a tridentate ligand coordinated to the platinum through atoms X, Y, and Z, respectively, wherein X and Y are nitrogen, Z is carbon, V represents O, S, N, C, P, or Si, and W is an anion.

2. The complex of claim 1, wherein W is a halogen, a cyano, alkyl, alkenyl, akynyl, alkoxy, alkylthio, amine, phosphine, or an optionally substituted aryl or heteroaryl group.

3. The complex of claim 1, wherein W is

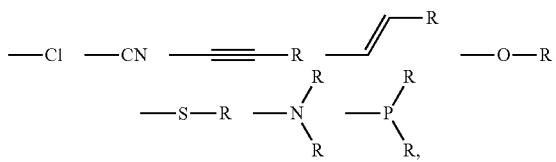

an unsubstituted aryl or heteroaryl group, or an aryl or heteroaryl group substituted with one or more R groups, wherein each R group independently represents an alkyl group, a haloalkyl group, an aralkyl group, an alkenyl group, alkynyl group, an aryl group, an amino group, a mono- or di-alkylamino group, a mono- or diaryl amino group, an alkoxy group, an aryloxy group, a heteroaryloxy group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, an ureido group, a phosphoramide group, a hydroxyl group, a mercapto group, a halogen atom, a cyano group, a sulfo group, a carboxyl group, a nitro group, a hydrazino group, a substituted silyl group, or a polymerizable group.

4. The complex of claim 1, wherein each of Ar1, Ar2, and Ar3 is independently unsubstituted or substituted with one more R groups, wherein each R group independently represents an alkyl group, a haloalkyl group, an aralkyl group, an alkenyl group, alkynyl group, an aryl group, an amino group, a mono- or di-alkylamino group, a mono- or diaryl amino group, an alkoxy group, an aryloxy group, a heteroaryloxy group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, an ureido group, a phosphoramide group, a hydroxyl group, a mercapto group, a halogen atom, a cyano group, a sulfo group, a carboxyl group, a nitro group, a hydrazino group, a substituted silyl group, or a polymerizable group.

5. The complex of claim 1, wherein —V— is selected from the group consisting of

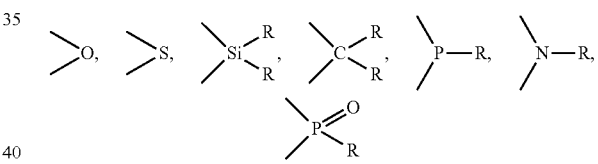

and any derivative thereof, wherein each R group independently represents an alkyl group, a haloalkyl group, an aralkyl group, an alkenyl group, alkenyl group, an aryl group, an amino group, a mono- or di-alkylamino group, a mono- or diaryl amino group, an alkoxy group, an aryloxy group, a heteroaryloxy group, an alkoxycarbonyl group, an acyloxy group, an acylamino group, an alkoxycarbonylamino group, an aryloxycarbonylamino group, a sulfonylamino group, a sulfamoyl group, a carbamoyl group, an alkylthio group, a sulfinyl group, an ureido group, a phosphoramide group, a hydroxyl group, a mercapto group, a halogen atom, a cyano group, a sulfo group, a carboxyl group, a nitro group, a hydrazino group, a substituted silyl group, or a polymerizable group.

6. A phosphorescent emitter comprising the complex of claim 1.

7. An organic light emitting device comprising the complex of claim 1.

* * * * *